US008404813B2

(12) United States Patent
Presta

(10) Patent No.: US 8,404,813 B2
(45) Date of Patent: Mar. 26, 2013

(54) ENGINEERED ANTI-IL-23P19 ANTIBODIES

(75) Inventor: Leonard G. Presta, San Francisco, CA (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 13/031,544

(22) Filed: Feb. 21, 2011

(65) Prior Publication Data
US 2011/0142853 A1 Jun. 16, 2011

Related U.S. Application Data

(63) Continuation of application No. 12/526,543, filed as application No. PCT/US2008/002333 on Feb. 21, 2008, now Pat. No. 8,293,883.

(60) Provisional application No. 60/891,409, filed on Feb. 23, 2007.

(51) Int. Cl.
C07K 16/00 (2006.01)
(52) U.S. Cl. .................................. 530/387.1; 424/130.1
(58) Field of Classification Search ........................ None
See application file for complete search history.

(56) References Cited

U.S. PATENT DOCUMENTS

| | | | |
|---|---|---|---|
| 4,816,397 A | 3/1989 | Boss et al. | |
| 4,816,567 A | 3/1989 | Cabilly et al. | |
| 6,096,289 A | 8/2000 | Goldenberg | |
| 6,495,667 B1 | 12/2002 | Bazan | |
| 6,610,285 B1 | 8/2003 | Hirata | |
| 7,090,847 B1 | 8/2006 | Oppmann et al. | |
| 7,608,690 B2 | 10/2009 | Bazan | |
| 2006/0063228 A1 | 3/2006 | Kasaian et al. | |
| 2006/0093600 A1 | 5/2006 | Bedian et al. | |
| 2006/0251658 A1 | 11/2006 | Ledbetter et al. | |
| 2007/0009526 A1 | 1/2007 | Benson et al. | |
| 2007/0048315 A1 | 3/2007 | Presta | |
| 2009/0123479 A1 | 5/2009 | Bembridge et al. | |

FOREIGN PATENT DOCUMENTS

| | | |
|---|---|---|
| EP | 0 438 310 A1 | 7/1991 |
| EP | 0 239 400 B1 | 8/1994 |
| WO | WO 00/53631 | 9/2000 |
| WO | WO 01/18051 | 3/2001 |
| WO | WO 2004/071517 | 8/2004 |
| WO | WO 2004/081190 | 9/2004 |
| WO | WO 2005/047324 | 5/2005 |
| WO | WO 2005/047326 | 5/2005 |
| WO | WO 2005/052157 | 6/2005 |
| WO | WO 2006/068987 | 6/2006 |
| WO | WO 2007/005955 | 1/2007 |
| WO | WO 2007/024846 | 3/2007 |
| WO | WO 2007/027714 | 3/2007 |
| WO | WO 2007/076524 | 7/2007 |
| WO | WO 2007/147019 | 12/2007 |
| WO | WO 2008/103432 | 8/2008 |
| WO | WO 2008/103473 | 8/2008 |
| WO | WO 2008/134659 | 11/2008 |
| WO | WO 2009/068627 | 6/2009 |
| WO | WO 2009/082624 | 7/2009 |

OTHER PUBLICATIONS

Aggarwal et al. (2003) *J. Biol. Chem.* 278(3):1910-1914, "Interleukin-23 promotes a distinct CD4 T cell activation state characterized by the production of interleukin-17".
Barbie & Lefranc (1998) *Experimental and Clinical Immunogenetics* 15:171-183, "The Human Immunoglobulin Kappa Variable (IGKV) Genes and Joining (IGKJ) Segments".
Beyer et al. (2008) *J. Mol. Biol.* 382:942-955, "Crystal structures of the pro-inflammatory cytokine Interleukin-23 and its complex with a high-affinity neutralizing antibody".
Bowman et al. (2006) *Curr. Opin. Infect. Dis.* 19(3):245-252, "Rationale and safety of anti-interleukin-23 and anti-interleukin-17A therapy".
Brorson et al. (1999) *J. Immunol.* 163:6694-6701, "Mutational Analysis of Avidity and Fine Specificity of Anti-Levan Antibodies".
Brummell et al. (1993) *Biochemistry* 32(4):1180-1187, "Probing the combining site of an anti-carbohydrate antibody by saturation-mutagenesis: role of the heavy-chain CDR3 residues".
Burks et al. (1997) *Proc. Natl. Acad. Sci. USA* 94(2):412-417, "In vitro scanning saturation mutagenesis of an antibody binding pocket".
Casset, et al. (2003) *BBRC* 307(1):198-205, "A peptide mimetic of an anti-CD4 monoclonal antibody by rational design".
Chen, et al. (1999) *J. Mol. Bio.* 293(4):865-881, "Selection and analysis of an optimized anti-VEGF antibody: crystal structure of an affinity-matured Fab in complex with antigen".
Chen et al. (2006) *J. Clin. Investigation* 116(5):1317-1326, "Anti-IL-23 therapy inhibits multiple inflammatory pathways and ameliorates autoimmune encephalomyelitis".
Chothia & Lesk (1987) *J. Mol. Biol.* 196: 901-917 "Canonical Structures for the Hypervariable Regions of Immunoglobulins".
Colman (1994) *Research in Immunol.* 145(1):33-36, "Effects of amino acid sequence changes on antibody-antigen interactions".
Cua & Kastelein (2006) *Nat. Immunol.* 7:557-559 "TGF-B, a 'double agent' in the immune pathology war".
Dall'Acqua (2006) *J. Immunol.* 177(2):1129-1138, "Modulation of the Effector Functions of a Human IgG1 through Engineering of Its Hinge Region".
Davies et al. (1996) *Immunotechnology* 2(3):169-179, "Affinity improvement of single antibody VH domains: residues in all three hypervariable regions affect antigen binding".
De Pascalis, et al. (2002) *The Journal of Immunology* 169(6):3076-3084, "Grafting of "Abbreviated" Complementarity-Determining Regions Containing Specificity-Determining Residues Essential for Ligand Contact to Engineer a Less Immunogenic Humanized Monoclonal Antibody".
Dennis (2006) *Nature* 442(7104):739-741, "Cancer: off by a whisker".

(Continued)

*Primary Examiner* — Laura B Goddard
*Assistant Examiner* — Meera Natarajan
(74) *Attorney, Agent, or Firm* — Gregory R. Bellomy

(57) ABSTRACT

Engineered antibodies to human IL-23p19 are provided, as well as uses thereof, e.g. in treatment of inflammatory, autoimmune, and proliferative disorders.

27 Claims, 2 Drawing Sheets

OTHER PUBLICATIONS

Dong (2006) *Nat. Rev. Immunol.* 6(4):329-333 "Diversification of T-helper-cell lineages: finding the family root of IL-17-producing cells".

Gorman et al. (1991) *Proc. Natl. Acad. Sci. USA* 88:4181 "Reshaping a therapeutic CD4 antibody".

Hodgson (1991) *Biotechnology (NY)* 9:421-5 "Making Monoclonals in Microbes".

Holm, et al. (2007) *Mol. Immunol.* 44(6):1075-1084, "Functional mapping and single chain construction of the anti-cytokeratin 8 monoclonal antibody TS1".

Holt et al. (2003) *Trends in Biotechnology* 21(11):484-490, "Domain antibodies: proteins for therapy".

Hunter (2005) *Nature Reviews—Immunology* 5:521-531, "New IL-12-family members: IL-23 and IL-27, cytokines with divergent functions".

Iwakura & Ishigame (2006) *J. Clin. Invest.* 116:1218-1222 "The IL-23/IL-17 axis in inflammation".

Jang, et al. (1998) *Molec. Immunol.* 35(18):1207-1217, "The structural basis for DNA binding by an anti-DNA autoantibody".

Jones et al. (1986) *Nature* 321:522-525 "Replacing the complementarity-determining regions in a human antibody with those from a mouse".

Kabat & Wu (1991) *J. Immunol.* 147:1709 "Identical V Region Amino Acid Sequences and Segments of Sequences in Antibodies of Different Specificities".

Kobayashi, et al. (1999) *Protein Engineering* 12(10):879-844, "Tryptophan H33 plays an important role in pyrimidine (6-4) pyrimidone photoproduct binding by a high-affinity antibody".

Kunkel (1985) *Proc. Natl. Acad. Sci. U.S.A* 82:488-492, "Rapid and efficient site-specific mutagenesis without phenotypic selection".

Lefranc (2001) *Experimental and Clinical Immunogenetics* 18:100-116, "Nomenclature of the Human Immunoglobulin Heavy (IGH) Genes".

Lefranc (2001) *Experimental and Clinical Immunogenetics* 18:161-174 "Nomenclature of the Human Immunoglobulin Kappa (IGK) Genes".

Little et al. (2000) *Immunology Today* 21(8):364-370, "Of mice and men: hybridoma and recombinant antibodies".

MacCallum, et al. (1996) *J. Mol. Biol.* 262(5):732-745, "Antibody-antigen interactions: contact analysis and binding site topography".

Morelli et al. (2005) *J. Immunol.* 175:7905-7915, "CD4+ T cell responses elicited by different subsets of human skin migratory dendritic cells".

Nestle et al. (2007) *Clin. Immunology* 123:S62-S63, "Evidence for a Role of the Interleukin-23 Pathway in the Pathogenesis of Psoriasis".

Oppmann, et al. (2000) *Immunity* 13:715-725 "Novel p19 Protein Engages IL-12p40 to Form a Cytokine, IL-23, with Biological Activities Similar as Well as Distinct from IL-12".

Parham, et al.(2002) *J Immunol* 168:5699-708 "A Receptor for the Heterodimeric Cytokine IL-23 Is Composed of IL-12RB1 and a Novel Cytokine Receptor Subunit, IL-23R".

Presta (1992) *Curr. Op. Struct. Biol.* 2(4):593-596, "Antibody Engineering".

Presta (2005) *J. Allergy Clin. Immunol.* 116:731-736, "Molecular mechanisms in allergy and clinical immunology: selection, design, and engineering of therapeutic antibodies".

Queen et al. (1989) *Proc. Natl. Acad. Sci. USA* 86:10029 "A humanized antibody that binds to the interleukin 2 receptor".

R&D Systems, *de nova: New Products from R&D Systems*, Mar. 2004, pp. 1-10.

R&D Systems, *de novo: New Products from R&D Systems*, Jun. 2005, pp. 1-12.

Reissner & Aswad (2003) *Cell. Mol. Life Sci.* 60(7):1281-1295, "Deamidation and isoaspartate formation in proteins: unwanted alterations or surreptitious signals?".

Riechmann et al. (1988) *Nature* 332:323-329 "Reshaping human antibodies for therapy".

Rudikoff, et al. (1982) *Proc. Natl. Acad. Sci. USA* 79:1979-1983 "Single amino acid substitution altering antigen-binding specificity".

Salfeld (2007) *Nature Biotech.* 25(12):1369-1372, "Isotype selection in antibody engineering".

Sehy, et al. (2005) *FASEB Journal* vol. 19, No. 4, Suppl. S, Part 1, pp. A945-A946 "Unambiguous detection of IL-23 (p19/p40) protein in native samples using a novel enzyme-linked immunosorbent assay".

Stumhofer et al. (2006) *Nature Immunol.* 7:937, "Interleukin 27 negatively regulates the development of interleukin 17-producing T helper cells during chronic inflammation of the central nervous system".

Tato & O'Shea (2006) *Nature* 441:166-168 "What does it mean to be just 17?".

Vajdos, et al. (2002) *J. Mol. Biol.* 320(2):415-428, "Comprehensive functional maps of the antigen-binding site of an anti-ErbB2 antibody obtained with shotgun scanning mutagenesis".

Veldhoen (2006) *Immunity* 24:179-189 TGFB in the Context of an Inflammatory Cytokine Milieu Supports De Novo Differentiation of IL-17-Producing T Cells.

Verhoeyen et al. (1988) *Science* 239:1534-1536 "Reshaping Human Antibodies: Grafting an Antilysozyme Activity".

Verreck et al. (2004) *PNAS* 101(13):4560-4565, "Human IL-23-producing type 1 macrophages promote but IL-10-producing type 2 macrophages subvert immunity to (myco)bacteria".

Voskoglou-Nomikos (2003) *Clin. Can. Res.* 9(11):4227-4239, Clinical predictive value of the in vitro cell line, human xenograft, and mouse allograft preclinical cancer models.

Wiekowski, et al. (2001) *J. Immunol.* 166:7563-7570 "Ubiquitous Transgenic Expression of the IL-23 Subunit p19 Induces Multiorgan Inflammation, Runting, Infertility, and Premature Death".

Wu, et al. (1999) *J. Mol. Biol.* 294:151-162 "Humanization of a murine monoclonal antibody by simultaneous optimization of framework and CDR residues".

```
                                          ---CDRH1--
m1A11   EVQLQQSGPELVKTGASVNISCKAS  GYSFTAYYIQ  WVKQSRGKSLEWIG
m11C1   HVQLQQSGPEVVRPGASVKLSCKAS  GYIFSAYWMT  WVKQRPGQGLEWIG
m5F5    QVQLQQSGAELARPGASVKLSCKAS  GYTFTSYGIS  WVKQRTGQDLEWIG
m21D1   QVQLQQSGLELVKPGSSLKISCKAS  GYSFTSFFIH  WLKQRPGQGLEWIG
m13B8   HVQLQQSGPELVRPGASVELSCKAS  GYIFITYWMT  WMKQRPGQGLEWIG
h13B8a  QVQLVQSGAEVKKPGASVKVSCKAS  GYIFITYWMT  WVRQAPGQGLEWMG
h13B8b  QVQLVQSGAEVKKPGASVKVSCKAS  GYIFITYWMT  WVRQAPGQGLEWMG
h13B8c  QVQLVQSGAEVKKPGASVKVSCKAS  GYIFITYWMT  WVRQAPGQGLEWMG

------CDRH2------
m1A11   YISCYNGATRYNQKFKG  KATFTVDTSSRTAYMQFSSLTSEDSAVYFCAR
m11C1   QIFPVRGSADYNEIFEG  KATLTVDTSSSTAYIQLSSLTSEDSAVYYCAR
m5F5    EIYPRSVNSYYNERFKG  KATLTADKSSSTAYMELRSLTSEDSAVYFCAR
m21D1   WIFPGNHDVEYNEKFKG  KATLTADTSSSTADMHLSSLTSEDSAVYFCAR
m13B8   QIFPASGSADYNEMFEG  KATLTVDTSSNTAYMQLSSLTSEDSAVYFCAR
h13B8a  QIFPASGSADYNEMFEG  RVTMTTDTSTSTAYMELRSLRSDDTAVYYCAR
h13B8b  QIFPASGSADYNEKFEG  RVTMTTDTSTSTAYMELRSLRSDDTAVYYCAR
h13B8c  QIFPASGSADYAQKLQG  RVTMTTDTSTSTAYMELRSLRSDDTAVYYCAR

-----CDRH3-----
m1A11   QGFYAMDY        WGQGTSVTVSS
m11C1   GGGGFAY         WGQGTLVTVSA
m5F5    GGNYYGRNYGDYFDY WGQGTTLTVSS
m21D1   GGGNL--------PY WGQGTLVTVSA
m13B8   GGGGFAY         WGQGTLVTVSA
h13B8a  GGGGFAY         WGQGTLVTVSS
h13B8b  GGGGFAY         WGQGTLVTVSS
h13B8c  GGGGFAY         WGQGTLVTVSS
```

FIG. 1

```
                                              ------CDRL1------
m1A11    NVVMTQTPLTLSVTIGQPASISC    KSSQSLLDSDGKT-YLN
m11C1    DIQMTQSPASLSASVGETVTITC    RASENIYS------YLA
m5F5     SQAVVTQESALTTSPGETVTLTC    RSSTGAVITSN---DAN
m21D1    DIQMTQSPSSLSASVGDRVTITC    RTSENIYS------YLA
m13B8    DIQMTQSPASLSASVGETVTITC    RTSENIYS------YLA
h13B8    DIQMTQSPSSLSASVGDRVTITC    RTSENIYS------YLA

-CDRL2-
m1A11    WLLQRPGQSPKRLIY    LVSKLDS    GVPDRFTGSGSGT
m11C1    WYQEKWGKSPQLLVY    NAKTLAE    GVPSRFSGSGSGT
m5F5     WVQEKPDHSFTGLIG    GTNNRAP    GVPARFSGSLIGD
m21D1    WYQQKPGKAPKLLIY    NAKTLAE    GVPSRFSGSGSGT
m13B8    WYQQKQGKSPQLLVY    NAKTLAE    GVPSRFSGSGSGT
h13B8    WYQQKPGKAPKLLIY    NAKTLAE    GVPSRFSGSGSGT

--CDRL3--
m1A11    DFTLKISRVEAEDLGLYYC    WQGTHFPFT    FGSGTKLEIKR
m11C1    QFSLKINSLQSEDFGSYYC    QHHYGTPFT    FGSGTKLEIKR
m5F5     KAALTITGAQTEDEAIYFC    ALWYSNHWV    FGGGTKLTVLG
m21D1    DFTLTISSLQPEDFATYYC    QHHYGIPFT    FGQGTKVEIKR
m13B8    QFSLKINRLQPEDFGRYFC    QHHYGIPFT    FGSGTKLEIKR
h13B8    DFTLTISSLQPEDFATYYC    QHHYGIPFT    FGQGTKVEIKR
```

FIG. 2

ENGINEERED ANTI-IL-23P19 ANTIBODIES

FIELD OF THE INVENTION

The present invention relates generally to interleukin-23 p19 (IL-23p19)-specific antibodies and uses thereof. More specifically, the invention relates to humanized antibodies that recognize human IL-23p19 and modulate its activity, particularly in inflammatory, autoimmune and proliferative disorders.

BACKGROUND OF THE INVENTION

The immune system functions to protect individuals from infective agents, e.g., bacteria, multi-cellular organisms, and viruses, as well as from cancers. This system includes several types of lymphoid and myeloid cells such as monocytes, macrophages, dendritic cells (DCs), eosinophils, T cells, B cells, and neutrophils. These lymphoid and myeloid cells often produce signaling proteins known as cytokines. The immune response includes inflammation, i.e., the accumulation of immune cells systemically or in a particular location of the body. In response to an infective agent or foreign substance, immune cells secrete cytokines which, in turn, modulate immune cell proliferation, development, differentiation, or migration. Immune response can produce pathological consequences, e.g., when it involves excessive inflammation, as in the autoimmune disorders (see, e.g., Abbas et al. (eds.) (2000) *Cellular and Molecular Immunology*, W.B. Saunders Co., Philadelphia, Pa.; Oppenheim and Feldmann (eds.) (2001) *Cytokine Reference*, Academic Press, San Diego, Calif.; von Andrian and Mackay (2000) *New Engl. J. Med.* 343:1020-1034; Davidson and Diamond (2001) *New Engl. J. Med.* 345:340-350).

Interleukin-12 (IL-12) is a heterodimeric molecule composed of p35 and p40 subunits. Studies have indicated that IL-12 plays a critical role in the differentiation of naïve T cells into T-helper type 1 CD4$^+$ lymphocytes that secrete IFNγ. It has also been shown that IL-12 is essential for T cell dependent immune and inflammatory responses in vivo. See, e.g., Cua et al. (2003) *Nature* 421:744-748. The IL-12 receptor is composed of IL-12β1 and IL-12β2 subunits.

Interleukin-23 (IL-23) is a heterodimeric cytokine comprised of two subunits, p19 which is unique to IL-23, and p40, which is shared with IL-12. The p19 subunit is structurally related to IL-6, granulocyte-colony stimulating factor (G-CSF), and the p35 subunit of IL-12. IL-23 mediates signaling by binding to a heterodimeric receptor, comprised of IL-23R and IL-12β1, which is shared by the IL-12 receptor. A number of early studies demonstrated that the consequences of a genetic deficiency in p40 (p40 knockout mouse; p40KO mouse) were more severe than those found in a p35KO mouse. Some of these results were eventually explained by the discovery of IL-23, and the finding that the p40KO prevents expression of not only IL-12, but also of IL-23 (see, e.g., Oppmann et al. (2000) *Immunity* 13:715-725; Wiekowski et al. (2001) *J. Immunol.* 166:7563-7570; Parham et al. (2002) *J. Immunol.* 168:5699-708; Frucht (2002) *Sci STKE* 2002, E1-E3; Elkins et al. (2002) *Infection Immunity* 70:1936-1948).

Recent studies, through the use of p40 KO mice, have shown that blockade of both IL-23 and IL-12 is an effective treatment for various inflammatory and autoimmune disorders. However, the blockade of IL-12 through p40 appears to have various systemic consequences such as increased susceptibility to opportunistic microbial infections. Bowman et al. (2006) *Curr. Opin. Infect. Dis.* 19:245.

Therapeutic antibodies may be used to block cytokine activity. The most significant limitation in using antibodies as a therapeutic agent in vivo is the immunogenicity of the antibodies. As most monoclonal antibodies are derived from rodents, repeated use in humans results in the generation of an immune response against the therapeutic antibody. Such an immune response results in a loss of therapeutic efficacy at a minimum and a potential fatal anaphylactic response at a maximum. Initial efforts to reduce the immunogenicity of rodent antibodies involved the production of chimeric antibodies, in which mouse variable regions were fused with human constant regions. Liu et al. (1987) *Proc. Natl. Acad. Sci. USA* 84:3439-43. However, mice injected with hybrids of human variable regions and mouse constant regions develop a strong anti-antibody response directed against the human variable region, suggesting that the retention of the entire rodent Fv region in such chimeric antibodies may still result in unwanted immunogenicity in patients.

It is generally believed that complementarity determining region (CDR) loops of variable domains comprise the binding site of antibody molecules. Therefore, the grafting of rodent CDR loops onto human frameworks (i.e., humanization) was attempted to further minimize rodent sequences. Jones et al. (1986) *Nature* 321:522; Verhoeyen et al. (1988) *Science* 239: 1534. However, CDR loop exchanges still do not uniformly result in an antibody with the same binding properties as the antibody of origin. Changes in framework residues (FR), residues involved in CDR loop support, in humanized antibodies also are required to preserve antigen binding affinity. Kabat et al. (1991) *J. Immunol.* 147:1709. While the use of CDR grafting and framework residue preservation in a number of humanized antibody constructs has been reported, it is difficult to predict if a particular sequence will result in the antibody with the desired binding, and sometimes biological, properties. See, e.g., Queen et al. (1989) *Proc. Natl. Acad. Sci. USA* 86:10029, Gorman et al. (1991) *Proc. Natl. Acad. Sci. USA* 88:4181, and Hodgson (1991) *Biotechnology (NY)* 9:421-5. Moreover, most prior studies used different human sequences for animal light and heavy variable sequences, rendering the predictive nature of such studies questionable. Sequences of known antibodies have been used or, more typically, those of antibodies having known X-ray structures, antibodies NEW and KOL. See, e.g., Jones et al., supra; Verhoeyen et al., supra; and Gorman et al., supra. Exact sequence information has been reported for a few humanized constructs. Exemplary engineered antibodies to IL-23p19 are disclosed in commonly-assigned U.S. Provisional Patent Application Nos. 60/891,409 and 60/891,413 (both filed 23 Feb. 2007), in U.S. Patent Application Publication Nos. 2007/0009526 and 2007/0048315, and in International Patent Publication Nos. WO 2007/076524, WO 2007/024846 and WO 2007/147019.

The need exists for anti-huIL-23p19 antibodies for use, e.g., in treatment of inflammatory, autoimmune, and proliferative disorders. Preferably, such antibodies are engineered to introduce human germline sequences to reduce immunogenicity in human subjects, e.g. in the framework regions. Preferably, such antibodies will have high affinity for huIL-23p19 and will bind with high specificity to huIL-23p19.

SUMMARY OF THE INVENTION

The present invention provides binding compounds, such as an antibodies or fragment thereof, including humanized or chimeric recombinant antibodies, that binds human IL-23p19, comprising an antibody light chain variable domain, or antigen binding fragment thereof, having at least one, two or three CDRs selected from the group consisting of SEQ ID NOs: 32-46. In one embodiment, the binding compound of the present invention comprises a light chain variable domain comprising at least one CDRL1 selected from the group consisting of SEQ ID NOs: 32-36; at least one CDRL2 selected from the group consisting of SEQ ID NOs: 37-41; and at least one CDRL3 selected from the group consisting of SEQ ID NOs: 42-46.

In one embodiment, the binding compound comprises an antibody heavy chain variable domain, or antigen binding fragment thereof, having at least one, two or three CDRs selected from the group consisting of SEQ ID NOs: 15-31. In one embodiment, the binding compound of the present invention comprises a heavy chain variable domain comprising at least one CDRH1 selected from the group consisting of SEQ ID NOs: 15-19; at least one CDRH2 selected from the group consisting of SEQ ID NOs: 20-26; and at least one CDRH3 selected from the group consisting of SEQ ID NOs: 27-31.

In other embodiments the binding compound of the present invention comprises a light chain variable domain and a heavy chain variable domain, or the antigen binding fragments thereof, described in the preceding two paragraphs.

In some embodiments, the binding compound comprises a framework region, wherein the amino acid sequence of the framework region is all or substantially all of a human immunoglobulin amino acid sequence.

In some embodiments the light chain and/or heavy chain variable domains comprise a variant of one or more of the CDRs. In various embodiments the variant domain comprises up to 1, 2, 3, 4, 5, 6, 7, 8, 9, 10 or more conservatively modified amino acid residues relative to the sequence of the respective SEQ ID NOs. Conservative amino acid substitutions are provided at Table 1.

In some embodiments the light chain variable domain comprises residues 1-108 of SEQ ID NO: 14 or a variant thereof. In some embodiments the heavy chain variable domain comprises a sequence selected from the group consisting of residues 1-116 of SEQ ID NOs: 6-8, such as SEQ ID NO: 6, SEQ ID NO: 7 or SEQ ID NO: 8. In various embodiments the variant variable domain comprises up to 1, 2, 3, 4, 5, 6, 7, 8, 9, 10, 15, 20, 30, 40 or 50 or more conservatively modified amino acid residues relative to the sequence of the respective SEQ ID NOs. In yet a further embodiment, the binding compound comprises a light chain variable domain and a heavy chain variable domain, or the antigen binding fragments thereof, described in this paragraph.

In one embodiment the binding compound comprises a light chain sequence of SEQ ID NO: 14 and/or a heavy chain sequence selected from the group consisting of SEQ ID NOs: 6-8.

In other embodiments the binding compound of the present invention comprises a light chain variable domain, or an antigen binding fragment thereof, consisting essentially of residues 1-108 of SEQ ID NO: 14, and/or a heavy chain variable domain, or an antigen binding fragment thereof, consisting essentially of a sequence selected from the group consisting of residues 1-116 of SEQ ID NOs: 6-8, such as SEQ ID NO: 6, SEQ ID NO: 7 or SEQ ID NO: 8.

In other embodiments the binding compound of the present invention comprises a light chain variable domain, or an antigen binding fragment thereof, having at least 50%, 75%, 80%, 85%, 90%, 95%, 98% or 99% sequence homology with residues 1-108 of SEQ ID NO: 14, and/or a heavy chain variable domain, or an antigen binding fragment thereof, having at least 50%, 75%, 80%, 85%, 90%, 95%, 98% or 99% sequence homology with a sequence selected from the group consisting of residues 1-116 of SEQ ID NOs: 6-8, such as SEQ ID NO: 6, SEQ ID NO: 7 or SEQ ID NO: 8.

In one embodiment, the binding compound of the present invention binds to human IL-23p19 (SEQ ID NO: 47) at an epitope comprising residues 20-30, or residues 82-110, or both. In another embodiment the IL-23p19 binding compound binds to an epitope comprising some or all of residues K20, T23, W26, S27, P30, E82, S95, L96, L97, P98, D99, P101, G103, Q104, H106, A107 and L110, and optionally residues L24, L85, T91, S100 and V102. In various embodiments the epitope for an antibody of interest is determined by obtaining an X-ray crystal structure of an antibody:antigen complex and determining which residues on IL-23p19 are within a specified distance of residues on the antibody of interest, wherein the specified distance is, e.g., 4 Å or 5 Å. In some embodiments, the epitope is defined as a stretch of 11 or more contiguous amino acid residues along the IL-23p19 sequence in which at least 30%, 40%, 45%, 50% or 54% of the residues are within the specified distance of the antibody.

In one embodiment, the invention relates to antibodies that are able to block the binding of a binding compound of the present invention to human IL-23 in a cross-blocking assay. In another embodiment, the invention relates to binding compounds that are able to block IL-23-mediated activity, such activities including but not limited to, binding to its receptor and promoting the proliferation or survival of $T_H17$ cells.

In some embodiments, the binding compound of the present invention further comprises a heavy chain constant region, wherein the heavy chain constant region comprises a γ1, γ2, γ3, or γ4 human heavy chain constant region or a variant thereof. In various embodiments the light chain constant region comprises a lambda or a kappa human light chain constant region.

In various embodiments the binding compounds of the present invention are polyclonal, monoclonal, chimeric, humanized or fully human antibodies or fragments thereof. The present invention also contemplates that the antigen binding fragment is an antibody fragment selected from the group consisting of, e.g., Fab, Fab', Fab'-SH, Fv, scFv, $F(ab')_2$, and a diabody.

The present invention encompasses a method of suppressing an immune response in a human subject comprising administering to a subject in need thereof an antibody (or a antigen binding fragment thereof) specific for IL-23 in an amount effective to block the biological activity of IL-23. In some embodiments, the antibody specific for IL-23 is the humanized or chimeric antibody. In further embodiments, the immune response is an inflammatory response including arthritis, psoriasis, and inflammatory bowel disease. In other embodiments, the immune response is an autoimmune response, including multiple sclerosis, uveitis, systemic lupus erythematosus and diabetes. In another embodiment, the subject has cancer and the immune response is a Th17 response.

The present invention also contemplates administering an additional immunosuppressive or anti-inflammatory agent. The binding compounds of the present invention can be in a pharmaceutical composition comprising the binding compound, or antigen binding fragment thereof, in combination with a pharmaceutically acceptable carrier or diluent. In a further embodiment, the pharmaceutical composition further comprises an immunosuppressive or anti-inflammatory agent.

The present invention encompasses an isolated nucleic acid encoding the polypeptide sequence of an antibody embodiment of the binding compound of the present invention. The nucleic acid can be in an expression vector operably linked to control sequences recognized by a host cell transfected with the vector. Also encompassed is a host cell comprising the vector, and a method of producing a polypeptide comprising culturing the host cell under conditions wherein the nucleic acid sequence is expressed, thereby producing the polypeptide, and recovering the polypeptide from the host cell or medium.

In various embodiments, the invention relates to use of a binding compound of the present invention in the manufacture of medicaments for the treatment of disorders including, but not limited to, inflammatory disease, autoimmune disease, cancer, infectious disease (e.g. bacterial, mycobacterial, viral or fungal infection, including chronic infections), arthritis, psoriasis, inflammatory bowel disease, multiple sclerosis, uveitis, systemic lupus erythematosus and diabetes.

In other embodiments the invention relates to pharmaceutical compositions comprising a binding compound of the present invention for treating disorders including, but not limited to, inflammatory disease, autoimmune disease, cancer, infectious disease (e.g. bacterial, mycobacterial, viral or fungal infection, including chronic infections), arthritis, psoriasis, inflammatory bowel disease, multiple sclerosis, uveitis, systemic lupus erythematosus and diabetes.

In some embodiments, the binding compound or pharmaceutical composition of the present invention induces a prolonged period of remission from disease symptoms in a subject, such that the dosing interval can be extended to much longer than the half-life of the binding compound in the subject, for example in the treatment of a relapsing-remitting disease. In various embodiments, the interval between one administration and another is 6-, 8-, 10-, 12-, 16-, 20-, 24-, 30-weeks or longer. In other embodiments a single administration is sufficient to permanently prevent relapses.

BRIEF DESCRIPTION OF THE DRAWINGS

FIG. 1 shows comparisons of mouse anti-human IL-23p19 antibody clone heavy chain variable domain sequences. Sequences are provided for clones m1A11, m11C1, m5F5, m21D1, m13B8, h13B8a, h13B8b and h13B8c. CDRs are indicated. In both figures, an "m" prefix connotes a murine antibody and an "h" connotes a humanized antibody. The suffixes "a", "b" and "c" refer to sequence variants of the humanized 13B8 heavy chain variable domain, as discussed in greater detail below.

FIG. 2 shows comparisons of mouse anti-human IL-23p19 antibody clone light chain variable domain sequences. Sequence are provided for clones m1A11, m11C1, m5F5, m21D1, m13B8, h13B8. CDRs are indicated.

DETAILED DESCRIPTION

As used herein, including the appended claims, the singular forms of words such as "a," "an," and "the," include their corresponding plural references unless the context clearly dictates otherwise. Table 7 below provides a listing of sequence identifiers used in this application. All references cited herein are incorporated by reference to the same extent as if each individual publication, patent application, or patent, was specifically and individually indicated to be incorporated by reference. Citation of the references herein is not intended as an admission that any of the foregoing is pertinent prior art, nor does it constitute any admission as to the contents or date of these publications or documents.

I. Definitions

"Proliferative activity" encompasses an activity that promotes, that is necessary for, or that is specifically associated with, e.g., normal cell division, as well as cancer, tumors, dysplasia, cell transformation, metastasis, and angiogenesis.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding composition, or by another cell. "Treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses contact of an agent with animal subject, a cell, tissue, physiological compartment, or physiological fluid. "Treatment of a cell" also encompasses situations where the agent contacts IL-23 receptor (IL-23R/IL-12Rbeta1 heterodimer), e.g., in the fluid phase or colloidal phase, but also situations where the agonist or antagonist does not contact the cell or the receptor.

As used herein, the term "antibody" refers to any form of antibody that exhibits the desired biological activity. Thus, it is used in the broadest sense and specifically covers monoclonal antibodies (including full length monoclonal antibodies), polyclonal antibodies, multispecific antibodies (e.g., bispecific antibodies), chimeric antibodies, humanized antibodies, fully human antibodies, etc. so long as they exhibit the desired biological activity.

As used herein, the terms "IL-23p19 binding fragment," "binding fragment thereof" or "antigen binding fragment thereof" encompass a fragment or a derivative of an antibody that still substantially retains its biological activity of inhibiting IL-23p19 activity. Therefore, the term "antibody fragment" or IL-23p19 binding fragment refers to a portion of a full length antibody, generally the antigen binding or variable region thereof. Examples of antibody fragments include Fab, Fab', F(ab')$_2$, and Fv fragments; diabodies; linear antibodies; single-chain antibody molecules, e.g., sc-Fv; and multispecific antibodies formed from antibody fragments. Typically, a binding fragment or derivative retains at least 10% of its IL-23p19 inhibitory activity. Preferably, a binding fragment or derivative retains at least 25%, 50%, 60%, 70%, 80%, 90%, 95%, 99% or 100% (or more) of its IL-23p19 inhibitory activity, although any binding fragment with sufficient affinity to exert the desired biological effect will be useful. It is also intended that a IL-23p19 binding fragment can include variants having conservative amino acid substitutions that do not substantially alter its biologic activity.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352: 624-628 and Marks et al. (1991) *J. Mol. Biol.* 222: 581-597, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. U.S. Pat. No. 4,816,567; Morrison et al. (1984) *Proc. Natl. Acad. Sci. USA* 81: 6851-6855.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific (see below).

As used herein, the term "single-chain Fv" or "scFv" antibody refers to antibody fragments comprising the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv, see Pluckthun (1994) THE PHARMACOLOGY OF MONOCLONAL ANTIBODIES, vol. 113, Rosenburg and Moore eds. Springer-Verlag, New York, pp. 269-315.

The monoclonal antibodies herein also include camelized single domain antibodies. See, e.g., Muyldermans et al. (2001) *Trends Biochem. Sci.* 26:230; Reichmann et al. (1999) *J. Immunol. Methods* 231:25; WO 94/04678; WO 94/25591; U.S. Pat. No. 6,005,079). In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) *Proc. Natl. Acad. Sci. USA* 90: 6444-6448. For a review of engineered antibody variants generally see Holliger and Hudson (2005) *Nat. Biotechnol.* 23:1126-1136.

As used herein, the term "humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum", "hu" or "h" is added to antibody clone designations when necessary to distinguish humanized antibodies (e.g. hum13B8) from parental rodent antibodies (e.g. mouse 13B8, or m13B8). The humanized forms of rodent antibodies will generally comprise the same CDR sequences of the parental rodent antibodies, although certain amino acid substitutions may be included to increase affinity, increase stability of the humanized antibody, or for other reasons.

The antibodies of the present invention also include antibodies with modified (or blocked) Fc regions to provide altered effector functions. See, e.g., U.S. Pat. No. 5,624,821; WO2003/086310; WO2005/120571; WO2006/0057702; Presta (2006) *Adv. Drug Delivery Rev.* 58:640-656. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies, and a longer half-life would result in less frequent dosing, with the concomitant increased convenience and decreased use of material. See Presta (2005) *J. Allergy Clin. Immunol.* 116:731 at 734-35.

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" refers to an antibody which comprises mouse immunoglobulin sequences only. A fully human antibody may be generated in a human being, in a transgenic animal having human immunoglobulin germline sequences, by phage display or other molecular biological methods.

As used herein, the term "hypervariable region" refers to the amino acid residues of an antibody that are responsible for antigen-binding. The hypervariable region comprises amino acid residues from a "complementarity determining region" or "CDR" (e.g. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain (Kabat et al. (1991) Sequences of Proteins of Immunological Interest, 5th Ed. Public Health Service, National Institutes of Health, Bethesda, Md.) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain (Chothia and Lesk (1987) *J. Mol. Biol.* 196: 901-917). As used herein, the term "framework" or "FR" residues refers to those variable domain residues other than the hypervariable region residues defined herein as CDR residues. The residue numbering above relates to the Kabat numbering system and does not necessarily correspond in detail to the sequence numbering in the accompanying Sequence Listing.

"Binding compound" refers to a molecule, small molecule, macromolecule, polypeptide, antibody or fragment or analogue thereof, or soluble receptor, capable of binding to a target. "Binding compound" also may refer to a complex of molecules, e.g., a non-covalent complex, to an ionized molecule, and to a covalently or non-covalently modified molecule, e.g., modified by phosphorylation, acylation, cross-linking, cyclization, or limited cleavage, which is capable of binding to a target. When used with reference to antibodies, the term "binding compound" refers to both antibodies and antigen binding fragments thereof. "Binding" refers to an association of the binding composition with a target where the association results in reduction in the normal Brownian motion of the binding composition, in cases where the binding composition can be dissolved or suspended in solution. "Binding composition" refers to a molecule, e.g. a binding compound, in combination with a stabilizer, excipient, salt, buffer, solvent, or additive, capable of binding to a target.

"Conservatively modified variants" or "conservative substitution" refers to substitutions of amino acids are known to those of skill in this art and may be made generally without altering the biological activity of the resulting molecule, even in essential regions of the polypeptide. Such exemplary substitutions are preferably made in accordance with those set forth in Table 1 as follows:

TABLE 1

Exemplary Conservative Amino Acid Substitutions

| Original residue | Conservative substitution |
|---|---|
| Ala (A) | Gly; Ser |
| Arg (R) | Lys, His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

In addition, those of skill in this art recognize that, in general, single amino acid substitutions in non-essential regions of a polypeptide do not substantially alter biological activity. See, e.g., Watson et al. (1987) *Molecular Biology of the Gene*, The Benjamin/Cummings Pub. Co., p. 224 (4th Edition).

The phrase "consists essentially of," or variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, a binding compound that consists essentially of a recited amino acid sequence may also include one or more amino acids, including substitutions of one or more amino acid residues, that do not materially affect the properties of the binding compound.

"Effective amount" encompasses an amount sufficient to ameliorate or prevent a symptom or sign of the medical condition. Effective amount also means an amount sufficient to allow or facilitate diagnosis. An effective amount for a particular patient or veterinary subject may vary depending on factors such as the condition being treated, the overall health of the patient, the method route and dose of administration and the severity of side affects. See, e.g., U.S. Pat. No. 5,888,530. An effective amount can be the maximal dose or dosing protocol that avoids significant side effects or toxic effects. The effect will result in an improvement of a diagnostic measure or parameter by at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%, where 100% is defined as the diagnostic parameter shown by a normal subject. See, e.g., Maynard et al. (1996) *A Handbook of SOPs for Good Clinical Practice*, Interpharm Press, Boca Raton, Fla.; Dent (2001) *Good Laboratory and Good Clinical Practice*, Urch Publ., London, UK.

"Immune condition" or "immune disorder" encompasses, e.g., pathological inflammation, an inflammatory disorder, and an autoimmune disorder or disease. "Immune condition" also refers to infections, persistent infections, and proliferative conditions, such as cancer, tumors, and angiogenesis, including infections, tumors, and cancers that resist eradication by the immune system. "Cancerous condition" includes, e.g., cancer, cancer cells, tumors, angiogenesis, and precancerous conditions such as dysplasia.

"Inflammatory disorder" means a disorder or pathological condition where the pathology results, in whole or in part, from, e.g., a change in number, change in rate of migration, or change in activation, of cells of the immune system. Cells of the immune system include, e.g., T cells, B cells, monocytes or macrophages, antigen presenting cells (APCs), dendritic cells, microglia, NK cells, NKT cells, neutrophils, eosinophils, mast cells, or any other cell specifically associated with the immunology, for example, cytokine-producing endothelial or epithelial cells.

An "IL-17-producing cell" means a T cell that is not a classical TH1-type T cell or classical TH2-type T cell, referred to as $T_H17$ cells. $T_H17$ cells are discussed in greater detail at Cua and Kastelein (2006) *Nat. Immunol.* 7:557-559; Tato and O'Shea (2006) *Nature* 441:166-168; Iwakura and Ishigame (2006) *J. Clin. Invest.* 116:1218-1222. "IL-17-producing cell" also means a T cell that expresses a gene or polypeptide of Table 10B of U.S. Patent Application Publication No. 2004/0219150 (e.g., mitogen responsive P-protein; chemokine ligand 2; interleukin-17 (IL-17); transcription factor RAR related; and/or suppressor of cytokine signaling 3), where expression with treatment by an IL-23 agonist is greater than treatment with an IL-12 agonist, where "greater than" is defined as follows. Expression with an IL-23 agonist is ordinarily at least 5-fold greater, typically at least 10-fold greater, more typically at least 15-fold greater, most typically at least 20-fold greater, preferably at least 25-fold greater, and most preferably at least 30-fold greater, than with IL-12 treatment. Expression can be measured, e.g., with treatment of a population of substantially pure IL-17 producing cells. A Th17 response is an immune response in which the activity and/or proliferation of Th17 cells are enhanced, typically coupled with a repressed Th1 response.

Moreover, "IL-17-producing cell" includes a progenitor or precursor cell that is committed, in a pathway of cell development or cell differentiation, to differentiating into an IL-17-producing cell, as defined above. A progenitor or precursor cell to the IL-17 producing cell can be found in a draining lymph node (DLN). Additionally, "IL-17-producing cell" encompasses an IL-17-producing cell, as defined above, that has been, e.g., activated, e.g., by a phorbol ester, ionophore, and/or carcinogen, further differentiated, stored, frozen, desiccated, inactivated, partially degraded, e.g., by apoptosis, proteolysis, or lipid oxidation, or modified, e.g., by recombinant technology.

As used herein, the term "isolated nucleic acid molecule" refers to a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, "polymerase chain reaction" or "PCR" refers to a procedure or technique in which minute amounts of a specific piece of nucleic acid, RNA and/or DNA, are amplified as described in, e.g., U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al. (1987) *Cold Spring Harbor Symp. Quant. Biol.* 51:263; Erlich, ed., (1989) PCR TECHNOLOGY (Stockton Press, N.Y.) As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

As used herein, the term "germline sequence" refers to a sequence of unrearranged immunoglobulin DNA sequences, including rodent (e.g. mouse) and human germline sequences. Any suitable source of unrearranged immunoglobulin DNA may be used. Human germline sequences may be obtained, for example, from JOINSOLVER® germline databases on the website for the National Institute of Arthritis and Musculoskeletal and Skin Diseases of the United States National Institutes of Health. Mouse germline sequences may be obtained, for example, as described in Giudicelli et al. (2005) *Nucleic Acids Res.* 33:D256-D261.

To examine the extent of inhibition of IL-23 activity, for example, samples or assays comprising a given, e.g., protein, gene, cell, or organism, are treated with a potential activating or inhibiting agent and are compared to control samples without the agent. Control samples, i.e., not treated with agent, are assigned a relative activity value of 100% Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 25%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Endpoints in activation or inhibition can be monitored as follows. Activation, inhibition, and response to treatment, e.g., of a cell, physiological fluid, tissue, organ, and animal or human subject, can be monitored by an endpoint. The endpoint may comprise a predetermined quantity or percentage of, e.g., an indicia of inflammation, oncogenicity, or cell degranulation or secretion, such as the release of a cytokine, toxic oxygen, or a protease. The endpoint may comprise, e.g., a predetermined quantity of ion flux or transport; cell migration; cell adhesion; cell proliferation; potential for metastasis; cell differentiation; and change in phenotype, e.g., change in expression of gene relating to inflammation, apoptosis, transformation, cell cycle, or metastasis (see, e.g., Knight (2000) *Ann. Clin. Lab. Sci.* 30:145-158; Hood and Cheresh (2002) *Nature Rev. Cancer* 2:91-100; Timme et al. (2003) *Curr. Drug Targets* 4:251-261; Robbins and Itzkowitz (2002) *Med. Clin. North Am.* 86:1467-1495; Grady and Markowitz (2002) *Annu. Rev. Genomics Hum. Genet.* 3:101-128; Bauer, et al. (2001) *Glia* 36:235-243; Stanimirovic and Satoh (2000) *Brain Pathol.* 10:113-126).

An endpoint of inhibition is generally 75% of the control or less, preferably 50% of the control or less, more preferably 25% of the control or less, and most preferably 10% of the control or less. Generally, an endpoint of activation is at least 150% the control, preferably at least two times the control, more preferably at least four times the control, and most preferably at least 10 times the control.

"Small molecule" is defined as a molecule with a molecular weight that is less than 10 kDa, typically less than 2 kDa, and preferably less than 1 kDa. Small molecules include, but are not limited to, inorganic molecules, organic molecules, organic molecules containing an inorganic component, molecules comprising a radioactive atom, synthetic molecules, peptide mimetics, and antibody mimetics. As a therapeutic, a small molecule may be more permeable to cells, less susceptible to degradation, and less apt to elicit an immune response than large molecules. Small molecules, such as peptide mimetics of antibodies and cytokines, as well as small molecule toxins are described. See, e.g., Casset et al. (2003) *Biochem. Biophys. Res. Commun.* 307:198-205; Muyldermans (2001) *J. Biotechnol.* 74:277-302; Li (2000) *Nat. Biotechnol.* 18:1251-1256; Apostolopoulos et al. (2002) *Curr. Med. Chem.* 9:411-420; Monfardini et al. (2002) *Curr. Pharm. Des.* 8:2185-2199; Domingues et al. (1999) *Nat. Struct. Biol.* 6:652-656; Sato and Sone (2003) *Biochem. J.* 371:603-608; U.S. Pat. No. 6,326,482.

"Specifically" or "selectively" binds, when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. As used herein, an antibody is said to bind specifically to a polypeptide comprising a given sequence (in this case IL-23p19) if it binds to polypeptides comprising the sequence of IL-23p19 but does not bind to proteins lacking the sequence of IL-23p19. For example, an antibody that specifically binds to a polypeptide comprising IL-23p19 may bind to a FLAG®-tagged form of IL-23p19 but will not bind to other FLAG®-tagged proteins.

The antibody, or binding composition derived from the antigen-binding site of an antibody, of the contemplated method binds to its antigen with an affinity that is at least two fold greater, preferably at least ten times greater, more preferably at least 20-times greater, and most preferably at least 100-times greater than the affinity with unrelated antigens. In a preferred embodiment the antibody will have an affinity that is greater than about $10^9$ liters/mol, as determined, e.g., by Scatchard analysis. Munsen et al. (1980) *Analyt. Biochem.* 107:220-239.

As used herein, the term "immunomodulatory agent" refers to natural or synthetic agents that suppress or modulate an immune response. The immune response can be a humoral or cellular response. Immunomodulatory agents encompass immunosuppressive or anti-inflammatory agents.

"Immunosuppressive agents," "immunosuppressive drugs," or "immunosuppressants" as used herein are therapeutics that are used in immunosuppressive therapy to inhibit or prevent activity of the immune system. Clinically they are used to prevent the rejection of transplanted organs and tissues (e.g. bone marrow, heart, kidney, liver), and/or in the treatment of autoimmune diseases or diseases that are most likely of autoimmune origin (e.g. rheumatoid arthritis, myasthenia gravis, systemic lupus erythematosus, ulcerative colitis, multiple sclerosis). Immunosuppressive drugs can be classified into four groups: glucocorticoids cytostatics; antibodies (including Biological Response Modifiers or DMARDs); drugs acting on immunophilins; other drugs, including known chemotherpeutic agents used in the treatment of proliferative disorders. For multiple sclerosis, in particular, the antibodies of the present invention can be administered in conjunction with a new class of myelin binding protein-like therapeutics, known as copaxones.

"Anti-inflammatory agents" or "anti-inflammatory drugs", is used to represent both steroidal and non-steroidal therapeutics. Steroids, also known as corticosteroids, are drugs that closely resemble cortisol, a hormone produced naturally by adrenal glands. Steroids are used as the main treatment for certain inflammatory conditions, such as: Systemic vasculitis (inflammation of blood vessels); and Myositis (inflammation of muscle). Steroids might also be used selectively to treat inflammatory conditions such as: rheumatoid arthritis (chronic inflammatory arthritis occurring in joints on both sides of the body); systemic lupus erythematosus (a generalized disease caused by abnormal immune system function); Sjögren's syndrome (chronic disorder that causes dry eyes and a dry mouth).

Non-steroidal anti-inflammatory drugs, usually abbreviated to NSAIDs, are drugs with analgesic, antipyretic and anti-inflammatory effects—they reduce pain, fever and inflammation. The term "non-steroidal" is used to distinguish these drugs from steroids, which (amongst a broad range of other effects) have a similar eicosanoid-depressing, anti-inflammatory action. NSAIDs are generally indicated for the symptomatic relief of the following conditions: rheumatoid arthritis; osteoarthritis; inflammatory arthropathies (e.g. ankylosing spondylitis, psoriatic arthritis, Reiter's syndrome); acute gout; dysmenorrhoea; metastatic bone pain; headache and migraine; postoperative pain; mild-to-moderate pain due to inflammation and tissue injury; pyrexia; and renal colic. NSAIDs include salicylates, arlyalknoic acids, 2-arylpropionic acids (profens), N-arylanthranilic acids (fenamic acids), oxicams, coxibs, and sulphonanilides.

II. General

The present invention provides engineered anti-IL-23 antibodies and uses thereof to treat inflammatory, autoimmune, and proliferative disorders.

A number of cytokines have a role in the pathology or repair of neurological disorders. IL-6, IL-17, interferon-gamma (IFNgamma, IFN-γ), and granulocyte colony-stimulating factor (GM-CSF) have been associated with multiple sclerosis. Matusevicius et al. (1999) *Multiple Sclerosis* 5:101-104; Lock et al. (2002) *Nature Med.* 8:500-508. IL-1alpha, IL-1beta, and transforming growth factor-beta 1 (TGF-beta1) play a role in ALS, Parkinson's disease, and Alzheimer's disease. Hoozemans et al. (2001) *Exp. Gerontol.* 36:559-570; Griffin and Mrak (2002) *J. Leukocyte Biol.* 72:233-238; Ilzecka et al. (2002) *Cytokine* 20:239-243. TNF-alpha, IL-1beta, IL-6, IL-8, interferon-gamma, and IL-17 appear to modulate response to brain ischemia. See, e.g., Kostulas et al. (1999) *Stroke* 30:2174-2179; Li et al. (2001) *J. Neuroimmunol.* 116:5-14. Vascular endothelial cell growth factor (VEGF) is associated with ALS. Cleveland and Rothstein (2001) *Nature* 2:806-819.

Inflammatory bowel disorders, e.g., Crohn's disease, ulcerative colitis, celiac disease, and irritable bowel syndrome, are mediated by cells of the immune system and by cytokines. For example, Crohn's disease is associated with increased IL-12 and IFNγ, while ulcerative colitis is associated with increased IL-5, IL-13, and transforming growth factor-beta (TGFbeta). IL-17 expression may also increase in Crohn's disease and ulcerative colitis. See, e.g., Podolsky (2002) *New Engl. J. Med.* 347:417-429; Bouma and Strober (2003) *Nat. Rev. Immunol.* 3:521-533; Bhan et al. (1999) *Immunol. Rev.* 169:195-207; Hanauer (1996) *New Engl. J. Med.* 334:841-848; Green (2003) *The Lancet* 362:383-391; McManus (2003) *New Engl. J. Med.* 348:2573-2574; Horwitz and Fisher (2001) *New Engl. J. Med.* 344:1846-1850; Andoh et al. (2002) *Int. J. Mol. Med.* 10:631-634; Nielsen et al. (2003) *Scand. J. Gastroenterol.* 38:180-185; Fujino et al. (2003) *Gut* 52:65-70.

IL-23 receptor is a heterodimeric complex of IL-23R and IL-12Rβ1 subunits. See Parham et al. (2000) *J. Immunol.*

168:5699. IL-12 receptor is a complex of IL-12Rβ1 and IL-12Rβ2 subunits. See Presky et al. (1996) *Proc. Nat'l Acad. Sci. USA* 93:14002. IL-23R has been implicated as a critical genetic factor in the inflammatory bowel disorders Crohn's disease and ulcerative colitis. Duerr et al. (2006) *Sciencexpress* 26 Oct. 2006:1. A genome-wide association study found that the gene for IL-23R was highly associated with Crohn's disease, with an uncommon coding variant (Arg381Gln) conferring strong protection against the disease. This genetic association confirms prior biological findings (Yen et al. (2006) *J. Clin. Investigation* 116:1218) suggesting that IL-23 and its receptor are promising targets for new therapeutic approached to treating IBD.

Inflammatory diseases of the skin, joints, CNS, as well as proliferative disorders elicit similar immune responses, thus IL-23 blockade should provide inhibition of these immune mediated inflammatory disorders, without comprising the host ability to fight systemic infections. Antagonizing IL-23 should relieve the inflammation associated with inflammatory bowel disease, Crohn's disease, Ulcerative Colitis, rheumatoid arthritis, psoriatic arthritis, psoriasis, ankylosing spondylitis, and atopic dermatitis. Use of IL-23 inhibitors will also provide inhibition of proliferative disorders, e.g., cancer and autoimmune disorders, e.g., multiple sclerosis, type I diabetes, and SLE. Descriptions of IL-23 in these various disorders can be found in the following published PCT applications: WO 04/081190; WO 04/071517; WO 00/53631; and WO 01/18051. IL-23 inhibitors may also find use in treatment of infections, including chronic infections, such as bacterial, mycobacterial, viral and fungal infections.

The p19 subunit of IL-23 is a member of the 'long chain' family of hematopoietic cytokines (Oppmann et al. (2000) supra) and comprises four packed α-helices termed A, B, C and D, with an up-up-down-down topology. The 4 helices are connected by 3 polypeptide loops. The A-B and C-D loops are modeled to be relatively long as they connect parallel helices. The short B-C loop connects the antiparallel B and C helices. The p19 subunit of IL-23 is a member of the IL-6 family of helical cytokines. This family of cytokines bind to their cognate receptors through three conserved epitopes (site I, II and III; Bravo and Heath (2000) *EMBO J.* 19:2399-2411). The p19 subunit interacts with three cytokine receptor subunits to form the competent signaling complex. When expressed in a cell, the p19 subunit first form a complex with the p40 subunit, which it shares with IL-12. As noted above, the p19p40 complex is secreted from the cell as a heterodimeric protein and is called IL-23. See, e.g., Oppmann et al., supra. The cellular receptor complex required to transduce the IL-23 signal consists of two members of the tall signaling receptor subunits of the IL-6/IL-12 family of cytokines, the IL-23-specific IL-23R (see, e.g., Parham et al., supra) and the IL-12Rb1, that is shared with IL-12.

Insights into the structural basis of 'long chain' cytokine/receptor recognition have shown that although large areas of protein surface are buried in formation of cytokine—receptor complexes, the affinity of the interaction is dominated by a few, often tightly clustered amino acid residues forming an energetic 'hot spot' in the center of the binding interface. The identity of the residues that dominate the binding energy of a large protein-protein interface has been termed the 'functional epitope.' The affinity of the interaction (and hence biological specificity) is consequently defined by the structural complementarity of the functional epitopes of ligand and receptor. Detailed mutagenesis studies have shown that the most significant residues that make up the functional epitopes of cytokines and receptors are hydrophobic contacts involving either non-polar side chains such as tryptophan, the aliphatic components of non-polar side chains or the polypeptide backbone. The non-polar 'core' is surrounded by a halo of polar residues of lesser importance for binding energy. Kinetic studies indicate that the primary role of the functional epitopes is to stabilize protein-protein interaction by decreasing the dissociation rate of the complex. It has been suggested that the initial contact between cytokine and receptor is dominated by random diffusion or 'rolling' of protein surfaces producing many unstable contacts. The complex is then stabilized when the functional epitopes of the receptor and ligand engage. See, e.g., Bravo and Heath, supra.

III. Generation of IL-23 Specific Antibodies

Any suitable method for generating monoclonal antibodies may be used. For example, a recipient may be immunized with a linked or unlinked (e.g. naturally occurring) form of the IL-23 heterodimer, or a fragment thereof. Any suitable method of immunization can be used. Such methods can include adjuvants, other immunostimulants, repeated booster immunizations, and the use of one or more immunization routes.

Any suitable source of IL-23 can be used as the immunogen for the generation of the non-human antibody, specific for the p 19 subunit, of the compositions and methods disclosed herein. Such forms include, but are not limited whole protein, including linked and naturally occurring heterodimers, peptide(s), and epitopes, generated through recombinant, synthetic, chemical or enzymatic degradation means known in the art.

Any form of the antigen can be used to generate the antibody that is sufficient to generate a biologically active antibody. Thus, the eliciting antigen may be a single epitope, multiple epitopes, or the entire protein alone or in combination with one or more immunogenicity enhancing agents known in the art. The eliciting antigen may be an isolated full-length protein, a cell surface protein (e.g., immunizing with cells transfected with at least a portion of the antigen), or a soluble protein (e.g., immunizing with only the extracellular domain portion of the protein). The antigen may be produced in a genetically modified cell. The DNA encoding the antigen may genomic or non-genomic (e.g., cDNA) and encodes at least a portion of the extracellular domain. As used herein, the term "portion" refers to the minimal number of amino acids or nucleic acids, as appropriate, to constitute an immunogenic epitope of the antigen of interest. Any genetic vectors suitable for transformation of the cells of interest may be employed, including but not limited to adenoviral vectors, plasmids, and non-viral vectors, such as cationic lipids.

Any suitable method can be used to elicit an antibody with the desired biologic properties to inhibit IL-23. It is desirable to prepare monoclonal antibodies (mAbs) from various mammalian hosts, such as mice, rodents, primates, humans, etc. Description of techniques for preparing such monoclonal antibodies may be found in, e.g., Stites et al. (eds.) BASIC AND CLINICAL IMMUNOLOGY (4th ed.) Lange Medical Publications, Los Altos, Calif., and references cited therein; Harlow and Lane (1988) ANTIBODIES: A LABORATORY MANUAL CSH Press; Goding (1986) MONOCLONAL ANTIBODIES: PRINCIPLES AND PRACTICE (2d ed.) Academic Press, New York, N.Y. Thus, monoclonal antibodies may be obtained by a variety of techniques familiar to researchers skilled in the art. Typically, spleen cells from an animal immunized with a desired antigen are immortalized, commonly by fusion with a myeloma cell. See Kohler and Milstein (1976) *Eur. J. Immunol.* 6:511-519. Alternative methods of immortalization include transformation with Epstein Barr Virus, oncogenes, or retroviruses, or other methods known in the art. See, e.g., Doyle et al. (eds. 1994 and periodic supplements) CELL AND TISSUE CULTURE:

LABORATORY PROCEDURES, John Wiley and Sons, New York, N.Y. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a antigen binding fragment thereof by screening a DNA library from human B cells according, e.g., to the general protocol outlined by Huse et al. (1989) Science 246:1275-1281.

Other suitable techniques involve selection of libraries of antibodies in phage or similar vectors. See, e.g., Huse et al. supra; and Ward et al. (1989) Nature 341:544-546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly U.S. Pat. No. 4,816,567; and Queen et al. (1989) Proc. Nat'l Acad. Sci. USA 86:10029-10033; or made in transgenic mice, see Mendez et al. (1997) Nature Genetics 15:146-156. See also Abgenix and Medarex technologies.

Antibodies or binding compositions against predetermined fragments of IL-23 can be raised by immunization of animals with conjugates of the polypeptide, fragments, peptides, or epitopes with carrier proteins. Monoclonal antibodies are prepared from cells secreting the desired antibody. These antibodies can be screened for binding to normal or defective IL-23. These monoclonal antibodies will usually bind with at least a $K_d$ of about 1 µM, more usually at least about 300 nM, 30 nM, 10 nM, 3 nM, 1 nM, 300 pM, 100 pM, 30 pM or better, usually determined by ELISA. Suitable non-human antibodies may also be identified using the biologic assays described in Examples 5 and 6, below.

A hybridoma expressing antibody 13B8 was deposited pursuant to the Budapest Treaty with American Type Culture Collection (ATCC—Manassas, Va., USA) on Aug. 17, 2006 under Accession Number PTA-7803.

IV. Humanization of IL-23 Specific Antibodies

Any suitable non-human antibody can be used as a source for the hypervariable region. Sources for non-human antibodies include, but are not limited to, murine, Lagomorphs (including rabbits), bovine, and primates. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance of the desired biological activity. For further details, see Jones et al. (1986) Nature 321:522-525; Reichmann et al. (1988) Nature 332:323-329; and Presta (1992) Curr. Op. Struct. Biol. 2:593-596.

Methods for recombinantly engineering antibodies have been described, e.g., by Boss et al. (U.S. Pat. No. 4,816,397), Cabilly et al. (U.S. Pat. No. 4,816,567), Law et al. (European Patent Application Publication No. EP438310A1) and Winter (European Patent No. EP239400B1).

Amino acid sequence variants of humanized anti-IL-23 antibody are prepared by introducing appropriate nucleotide changes into the humanized anti-IL-23 antibody DNA, or by peptide synthesis. Such variants include, for example, deletions from, and/or insertions into, and/or substitutions of, residues within the amino acid sequences shown for the humanized anti-IL-23 antibody. Any combination of deletion, insertion, and substitution is made to arrive at the final construct, provided that the final construct possesses the desired characteristics. The amino acid changes also may alter post-translational processes of the humanized anti-IL-23 antibody, such as changing the number or position of glycosylation sites.

A useful method for identification of certain residues or regions of the humanized anti-IL-23p19 antibody polypeptide that are preferred locations for mutagenesis is called "alanine scanning mutagenesis," as described by Cunningham and Wells (1989) Science 244: 1081-1085. Here, a residue or group of target residues are identified (e.g., charged residues such as Arg, Asp, His, Lys, and Glu) and replaced by a neutral or negatively charged amino acid (most preferably alanine or polyalanine) to affect the interaction of the amino acids with IL-23 antigen. The amino acid residues demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, Ala scanning or random mutagenesis is conducted at the target codon or region and the expressed humanized anti-IL-23p19 antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include humanized anti-IL-23 antibody with an N-terminal methionyl residue or the antibody fused to an epitope tag. Other insertional variants of the humanized anti-IL-23 antibody molecule include the fusion to the N- or C-terminus of humanized anti-IL-23 antibody of an enzyme or a polypeptide which increases the serum half-life of the antibody.

Another type of variant is an amino acid substitution variant. These variants have at least one amino acid residue in the humanized anti-IL-23p19 antibody molecule removed and a different residue inserted in its place. The sites of greatest interest for substitutional mutagenesis include the hypervariable loops, but FR alterations are also contemplated.

Another type of amino acid variant of the antibody alters the original glycosylation pattern of the antibody. By altering is meant deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Yet another type of amino acid variant is the substitution of residues to provide for greater chemical stability of the final humanized antibody. For example, an asparagine (N) residue may be changed to reduce the potential for formation of isoaspartate at any NG sequences within a rodent CDR. A similar problem may occur at a DG sequence. Reissner and Aswad (2003) Cell. Mol. Life. Sci. 60:1281. Isoaspartate formation may debilitate or completely abrogate binding of an antibody to its target antigen. Presta (2005) J. Allergy Clin. Immunol. 116:731 at 734. In one embodiment, the asparagine is changed to glutamine (Q). In addition, methionine residues in rodent CDRs may be changed to reduce the possibility that the methionine sulfur would oxidize, which could reduce antigen binding affinity and also contribute to molecular heterogeneity in the final antibody preparation. Id. In one embodiment, the methionine is changed to alanine (A). Antibodies with such substitutions are subsequently screened to ensure that the substitutions do not decrease IL-23p19 binding affinity to unacceptable levels.

Nucleic acid molecules encoding amino acid sequence variants of humanized IL-23 specific antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of humanized anti-IL-23p19 antibody.

Ordinarily, amino acid sequence variants of the humanized anti-IL-23 antibody will have an amino acid sequence having at least 75% amino acid sequence identity with the original humanized antibody amino acid sequences of either the heavy or the light chain more preferably at least 80%, more preferably at least 85%, more preferably at least 90%, and most preferably at least 95, 98, or 99%. Identity or homology with respect to this sequence is defined herein as the percentage of amino acid residues in the candidate sequence that are identical with the humanized anti-IL-23 residues, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the antibody sequence shall be construed as affecting sequence identity or homology.

The humanized antibody can be selected from any class of immunoglobulins, including IgM, IgG, IgD, IgA, and IgE. Preferably, the antibody is an IgG antibody. Any isotype of IgG can be used, including $IgG_1$, $IgG_2$, $IgG_3$, and $IgG_4$. Variants of the IgG isotypes are also contemplated. The humanized antibody may comprise sequences from more than one class or isotype. Optimization of the necessary constant domain sequences to generate the desired biologic activity is readily achieved by screening the antibodies in the biological assays described below.

Likewise, either class of light chain can be used in the compositions and methods herein. Specifically, kappa, lambda, or variants thereof are useful in the present compositions and methods.

Any suitable portion of the CDR sequences from the non-human antibody can be used. The CDR sequences can be mutagenized by substitution, insertion or deletion of at least one residue such that the CDR sequence is distinct from the human and non-human antibody sequence employed. It is contemplated that such mutations would be minimal. Typically, at least 75% of the humanized antibody residues will correspond to those of the non-human CDR residues, more often 90%, and most preferably greater than 95%.

Any suitable portion of the FR sequences from the human antibody can be used. The FR sequences can be mutagenized by substitution, insertion or deletion of at least one residue such that the FR sequence is distinct from the human and non-human antibody sequence employed. It is contemplated that such mutations would be minimal. Typically, at least 75% of the humanized antibody residues will correspond to those of the human FR residues, more often 90%, and most preferably greater than 95, 98, or 99%.

CDR and FR residues are determined according to the standard sequence definition of Kabat. Kabat et al. (1987) Sequences of Proteins of Immunological Interest, National Institutes of Health, Bethesda Md. SEQ ID NOs: 1-5 show the heavy chain variable domain sequences of various mouse anti-human IL-23p19 antibodies, and SEQ ID NOs: 9-13 depict the light chain variable domain sequences. FIGS. 1 and 2 provide sequence lineups of heavy and light chain variable domains of the various antibodies of the present invention. CDRs are indicated in the figures, and the individual CDR sequences are each presented with unique Sequence Identifiers as indicated in Table 7.

Humanized forms of antibody 13B8 are provided. The humanized light chain 13B8 sequence (with kappa constant region) is provided at SEQ ID NO: 14, and the light chain variable domain comprises residues 1-108 of that sequence. Three versions of the humanized heavy chain 13B8 sequence (with γ1 constant regions) are provided at SEQ ID NOs: 6-8, and the heavy chain variable domain comprises residues 1-116 of those sequences. The 13B8 heavy chains variants are illustrated at Table 2, with differences from the parental sequence noted in bold. The Met (M) was modified to Lys (K) to avoid the potential for oxidation of the residue and inactivation of the antibody. The substitution of AQKLQ for NEMFE is a replacement of the murine CDR sequence with the human germline sequence from the human framework selected to humanize the antibody.

TABLE 2

Antibody 13B8 CDRH2 Variants

| Antibody | CDRH2 Sequence | SEQ ID NO: |
|---|---|---|
| m13B8, h13B8-a | QIFPASGSA DYNEMFEG | 24 |
| h13B8-b | QIFPASGSA DYNEKFEG | 25 |
| h13B8-c | QIFPASGSA DYAQKLQG | 26 |

Humanized forms of the other antibodies disclosed herein may be created by simply substituting the parental rodent antibody CDRs into the light and heavy chain sequences for humanized 13B8 provided at SEQ ID NOs: 14 and 6. This approach is most likely to be successful for antibody chains with CDRs having high homology with the CDRs of antibody 13B8, e.g. clone 11C1 on the heavy chain and clones 11C1 and 21D1 on the light chain. Alternatively, the murine antibodies may be independently humanized using the approaches outlines herein, e.g. at Example 2.

In one embodiment, CDRs include variants of any single sequence CDR disclosed herein (SEQ ID NOs: 15-46), in which the variant comprises 1, 2, 3, 4, 5, 6, 7, 8, 9, 10 or more conservative amino acid substitutions relative to the disclosed sequence, as determined using the data of Table 1.

Also contemplated are chimeric antibodies. As noted above, typical chimeric antibodies comprise a portion of the heavy and/or light chain identical with, or homologous to, corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. See U.S. Pat. No. 4,816,567; and Morrison et al. (1984) *Proc. Natl. Acad. Sci. USA* 81: 6851-6855.

Bispecific antibodies are also useful in the present methods and compositions. As used herein, the term "bispecific antibody" refers to an antibody, typically a monoclonal antibody, having binding specificities for at least two different antigenic epitopes, e.g., IL-23p19 and IL-17. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al. (1983) *Nature* 305: 537-39. Alternatively, bispecific antibodies can be prepared using chemical linkage. See, e.g., Brennan et al. (1985) *Science* 229:81. Bispecific antibodies include bispecific antibody fragments. See, e.g., Holliger et al. (1993) *Proc. Natl. Acad. Sci. U.S.A.* 90:6444-48, Gruber et al. (1994) *J. Immunol.* 152:5368.

In yet other embodiments, different constant domains may be appended to the humanized $V_L$ and $V_H$ regions provided herein. For example, if a particular intended use of an antibody (or fragment) of the present invention were to call for altered effector functions, a heavy chain constant domain other than IgG1 may be used. Although IgG1 antibodies provide for long half-life and for effector functions, such as complement activation and antibody-dependent cellular cytotoxicity, such activities may not be desirable for all uses of the antibody. In such instances an IgG4 constant domain, for example, may be used.

V. Biological Activity of Humanized Anti-IL-23

Antibodies having the characteristics identified herein as being desirable in a humanized anti-IL-23 antibody can be screened for inhibitory biologic activity in vitro or suitable binding affinity. To screen for antibodies that bind to the epitope on human IL-23 (i.e. the p19 subunit) bound by an antibody of interest (e.g., those that block binding of the cytokine to its receptor), a routine cross-blocking assay such as that described in ANTIBODIES, A LABORATORY MANUAL, Cold Spring Harbor Laboratory, Ed Harlow and David Lane (1988), can be performed. Antibodies that bind to the same epitope are likely to cross-block in such assays, but not all cross-blocking antibodies will necessarily bind at precisely the same epitope since cross-blocking may result from steric hindrance of antibody binding by antibodies bind at overlapping epitopes, or even nearby non-overlapping epitopes.

Alternatively, epitope mapping, e.g., as described in Champe et al. (1995) *J. Biol. Chem.* 270:1388-1394, can be performed to determine whether the antibody binds an epitope of interest. "Alanine scanning mutagenesis," as described by Cunningham and Wells (1989) *Science* 244: 1081-1085, or some other form of point mutagenesis of amino acid residues in human IL-23 may also be used to determine the functional epitope for an anti-IL-23 antibody of the present invention. Mutagenesis studies, however, may also reveal amino acid residues that are crucial to the overall three-dimensional structure of IL-23 but that are not directly involved in antibody-antigen contacts, and thus other methods may be necessary to confirm a functional epitope determined using this method.

The epitope bound by a specific antibody may also be determined by assessing binding of the antibody to peptides comprising fragments of human IL-23p19 (SEQ ID NO: 47). The sequence of the p40 subunit of IL-12 and IL-23 is found at GenBank Accession No. P29460. A series of overlapping peptides encompassing the sequence of IL-23p19 may be synthesized and screened for binding, e.g. in a direct ELISA, a competitive ELISA (where the peptide is assessed for its ability to prevent binding of an antibody to IL-23p19 bound to a well of a microtiter plate), or on a chip. Such peptide screening methods may not be capable of detecting some discontinuous functional epitopes, i.e. functional epitopes that involve amino acid residues that are not contiguous along the primary sequence of the IL-23p19 polypeptide chain.

The epitope bound by antibodies of the present invention may also be determined by structural methods, such as X-ray crystal structure determination (e.g., WO2005/044853), molecular modeling and nuclear magnetic resonance (NMR) spectroscopy, including NMR determination of the H-D exchange rates of labile amide hydrogens in IL-23 when free and when bound in a complex with an antibody of interest (Zinn-Justin et al. (1992) *Biochemistry* 31:11335-11347; Zinn-Justin et al. (1993) *Biochemistry* 32:6884-6891).

With regard to X-ray crystallography, crystallization may be accomplished using any of the known methods in the art (e.g. Giege et al. (1994) *Acta Crystallogr.* D50:339-350; McPherson (1990) *Eur. J. Biochem.* 189:1-23), including microbatch (e.g. Chayen (1997) *Structure* 5:1269-1274), hanging-drop vapor diffusion (e.g. McPherson (1976) *J. Biol. Chem.* 251:6300-6303), seeding and dialysis. It is desirable to use a protein preparation having a concentration of at least about 1 mg/mL and preferably about 10 mg/mL to about 20 mg/mL. Crystallization may be best achieved in a precipitant solution containing polyethylene glycol 1000-20,000 (PEG; average molecular weight ranging from about 1000 to about 20,000 Da), preferably about 5000 to about 7000 Da, more preferably about 6000 Da, with concentrations ranging from about 10% to about 30% (w/v). It may also be desirable to include a protein stabilizing agent, e.g. glycerol at a concentration ranging from about 0.5% to about 20%. A suitable salt, such as sodium chloride, lithium chloride or sodium citrate may also be desirable in the precipitant solution, preferably in a concentration ranging from about 1 mM to about 1000 mM. The precipitant is preferably buffered to a pH of from about 4.0 to about 10.0, often from about 7.0 to 8.5, e.g. pH 8.0. Specific buffers useful in the precipitant solution may vary and are well-known in the art. Scopes, Protein Purification: Principles and Practice, Third ed., (1994) Springer-Verlag, New York. Examples of useful buffers include, but are not limited to, HEPES, Tris, MES and acetate. Crystals may be grow at a wide range of temperatures, including 2° C., 4° C., 8° C. and 26° C.

Antibody:antigen crystals may be studied using well-known X-ray diffraction techniques and may be refined using computer software such as X-PLOR (Yale University, 1992, distributed by Molecular Simulations, Inc.; see e.g. Blundell & Johnson (1985) *Meth. Enzymol.* 114 & 115, H. W. Wyckoff et al. eds., Academic Press; U.S. Patent Application Publication No. 2004/0014194), and BUSTER (Bricogne (1993) *Acta Cryst. D*49:37-60; Bricogne (1997) *Meth. Enzymol.* 276A:361-423, Carter & Sweet, eds.; Roversi et al. (2000) *Acta Cryst. D*56:1313-1323).

Additional antibodies binding to the same epitope as an antibody of the present invention may be obtained, for example, by screening of antibodies raised against IL-23 for binding to the epitope, or by immunization of an animal with a peptide comprising a fragment of human IL-23 comprising the epitope sequence. Antibodies that bind to the same functional epitope might be expected to exhibit similar biological activities, such as blocking receptor binding, and such activities can be confirmed by functional assays of the antibodies.

Antibody affinities (e.g. for human IL-23) may be determined using standard analysis. Preferred humanized antibodies are those which bind human IL-23p19 with a $K_d$ value of no more than about $1 \times 10^{-7}$; preferably no more than about $1 \times 10^{-8}$; more preferably no more than about $1 \times 10^{-9}$; and most preferably no more than about $1 \times 10^{-10}$ or even $1 \times 10^{-11}$ M.

The antibodies and fragments thereof useful in the present compositions and methods are biologically active antibodies and fragments. As used herein, the term "biologically active" refers to an antibody or antibody fragment that is capable of binding the desired the antigenic epitope and directly or indirectly exerting a biologic effect. Typically, these effects result from the failure of IL-23 to bind its receptor. As used herein, the term "specific" refers to the selective binding of the antibody to the target antigen epitope. Antibodies can be tested for specificity of binding by comparing binding to IL-23 to binding to irrelevant antigen or antigen mixture under a given set of conditions. If the antibody binds to IL-23 at least 10, and preferably 50 times more than to irrelevant antigen or antigen mixture then it is considered to be specific. An antibody that binds to IL-12 is not an IL-23-specific antibody. An antibody that "specifically binds" to IL-23p19 does not bind to proteins that do not comprise the IL-23p19-derived sequences, i.e. "specificity" as used herein relates to IL-23p19 specificity, and not any other sequences that may be present in the protein in question. For example, as used herein, an antibody that "specifically binds" to IL-23p19 will typically bind to FLAG®-hIL-23p19, which is a fusion protein comprising IL-23p19 and a FLAG® peptide tag, but it does not bind to the FLAG® peptide tag alone or when it is fused to a protein other than IL-23p19.

IL-23-specific binding compounds of the present invention, such as inhibitory IL-23p19 specific antibodies, can inhibit its biological activity in any manner, including but not limited to production of IL-1β and TNF by peritoneal macrophages and IL-17 by $T_H17$ T cells. See Langrish et al. (2004) *Immunol. Rev.* 202:96-105. Anti-IL-23p19 antibodies will also be able to inhibit the gene expression of IL-17A, IL-17F, CCL7, CCL17, CCL20, CCL22, CCR1, and GM-CSF. See Langrish et al. (2005) *J. Exp. Med.* 201:233-240. IL-23-specific binding compounds of the present invention, such as anti IL-23p19 antibodies, will also block the ability of IL-23 to enhance proliferation or survival of $T_H17$ cells. Cua and Kastelein (2006) *Nat. Immunol.* 7:557-559. The inhibitory activity of engineered anti-IL-23p19 will be useful in the treatment of inflammatory, autoimmune, and proliferative disorders. Examples of such disorders are described in PCT patent application publications WO 04/081190; WO 04/071517; WO 00/53631; and WO 01/18051.

VI. Pharmaceutical Compositions

To prepare pharmaceutical or sterile compositions including IL-23p19 antibody, the cytokine analogue or mutein, antibody thereto, or nucleic acid thereof, is admixed with a pharmaceutically acceptable carrier or excipient. See, e.g., *Remington's Pharmaceutical Sciences* and *U.S. Pharmacopeia: National Formulary*, Mack Publishing Company, Easton, Pa. (1984).

Formulations of therapeutic and diagnostic agents may be prepared by mixing with physiologically acceptable carriers, excipients, or stabilizers in the form of, e.g., lyophilized powders, slurries, aqueous solutions or suspensions. See, e.g., Hardman et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis et al. (eds.) (1993) *Pharmaceutical Dosage Forms Parenteral Medications*, Marcel Dekker, NY; Lieberman, et al. (eds.) (1990) *Pharmaceutical Dosage Forms: Tablets*, Marcel Dekker, NY; Lieberman et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.

Toxicity and therapeutic efficacy of the antibody compositions, administered alone or in combination with an immunosuppressive agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio of $LD_{50}$ to $ED_{50}$. Antibodies exhibiting high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

The mode of administration is not particularly important. Suitable routes of administration may, for example, include oral, rectal, transmucosal, or intestinal administration; parenteral delivery, including intramuscular, intradermal, subcutaneous, intramedullary injections, as well as intrathecal, direct intraventricular, intravenous, intraperitoneal, intranasal, or intraocular injections. Administration of antibody used in the pharmaceutical composition or to practice the method of the present invention can be carried out in a variety of conventional ways, such as oral ingestion, inhalation, topical application or cutaneous, subcutaneous, intraperitoneal, parenteral, intraarterial or intravenous injection.

Alternately, one may administer the antibody in a local rather than systemic manner, for example, via injection of the antibody directly into an arthritic joint or pathogen-induced lesion characterized by immunopathology, often in a depot or sustained release formulation. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

Selecting an administration regimen for a therapeutic depends on several factors, including the serum or tissue turnover rate of the entity, the level of symptoms, the immunogenicity of the entity, and the accessibility of the target cells in the biological matrix. Preferably, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available. See, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert et al. (2003) New Engl. J. Med. 348: 601-608; Milgrom et al. (1999) New Engl. J. Med. 341:1966-1973; Slamon et al. (2001) New Engl. J. Med. 344:783-792; Beniaminovitz et al. (2000) New Engl. J. Med. 342:613-619; Ghosh et al. (2003) New Engl. J. Med. 348:24-32; Lipsky et al. (2000) New Engl. J. Med. 343:1594-1602.

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Preferably, a biologic that will be used is substantially derived from the same species as the animal targeted for treatment (e.g. a humanized antibody for treatment of human subjects), thereby minimizing any immune response to the reagent.

Antibodies, antibody fragments, and cytokines can be provided by continuous infusion, or by doses at intervals of, e.g., one day, 1-7 times per week, one week, two weeks, monthly, bimonthly, etc. Doses may be provided intravenously, subcutaneously, topically, orally, nasally, rectally, intramuscular, intracerebrally, intraspinally, or by inhalation. A preferred dose protocol is one involving the maximal dose or dose frequency that avoids significant undesirable side effects. A total weekly dose is generally at least 0.05 µg/kg, 0.2 µg/kg, 0.5 µg/kg, 1 µg/kg, 10 µg/kg, 100 µg/kg, 0.2 mg/kg, 1.0 mg/kg, 2.0 mg/kg, 10 mg/kg, 25 mg/kg, 50 mg/kg body weight or more. See, e.g., Yang et al. (2003) New Engl. J. Med. 349:427-434; Herold et al. (2002) New Engl. J. Med. 346:1692-1698; Liu et al. (1999) J. Neurol. Neurosurg. Psych. 67:451-456; Portielji et al. (20003) Cancer Immunol. Immunother. 52:133-144. The desired dose of a small molecule therapeutic, e.g., a peptide mimetic, natural product, or organic chemical, is about the same as for an antibody or polypeptide, on a moles/kg basis.

As used herein, "inhibit" or "treat" or "treatment" includes a postponement of development of the symptoms associated with autoimmune disease or pathogen-induced immunopathology and/or a reduction in the severity of such symptoms that will or are expected to develop. The terms further include ameliorating existing uncontrolled or unwanted autoimmune-related or pathogen-induced immunopathology symptoms, preventing additional symptoms, and ameliorating or preventing the underlying causes of such symptoms. Thus, the terms denote that a beneficial result has been conferred on a vertebrate subject with an autoimmune or pathogen-induced immunopathology disease or symptom, or with the potential to develop such a disease or symptom.

As used herein, the term "therapeutically effective amount" or "effective amount" refers to an amount of an IL-23p19 specific binding compound, e.g. and antibody, that when administered alone or in combination with an additional therapeutic agent to a cell, tissue, or subject is effective to prevent or ameliorate the autoimmune disease or pathogen-induced immunopathology associated disease or condition or the progression of the disease. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of therapeutic will decrease the symptoms typically by at least 10%; usually by at least 20%; preferably at least about 30%; more preferably at least 40%, and most preferably by at least 50%.

Methods for co-administration or treatment with a second therapeutic agent, e.g., a cytokine, antibody, steroid, chemotherapeutic agent, antibiotic, or radiation, are well known in the art, see, e.g., Hardman et al. (eds.) (2001) *Goodman and Gilman's The Pharmacological Basis of Therapeutics*, $10^{th}$ ed., McGraw-Hill, New York, N.Y.; Poole and Peterson (eds.) (2001) *Pharmacotherapeutics for Advanced Practice: A Practical Approach*, Lippincott, Williams & Wilkins, Phila., PA; Chabner and Longo (eds.) (2001) *Cancer Chemotherapy and Biotherapy*, Lippincott, Williams & Wilkins, Phila., PA. The pharmaceutical composition of the invention may also contain other immunosuppressive or immunomodulating agents. Any suitable immunosuppressive agent can be employed, including but not limited to anti-inflammatory agents, corticosteroids, cyclosporine, tacrolimus (i.e., FK-506), sirolimus, interferons, soluble cytokine receptors (e.g., sTNRF and sIL-1R), agents that neutralize cytokine activity (e.g., inflixmab, etanercept), mycophenolate mofetil, 15-deoxyspergualin, thalidomide, glatiramer, azathioprine, leflunomide, cyclophosphamide, methotrexate, and the like. The pharmaceutical composition can also be employed with other therapeutic modalities such as phototherapy and radiation.

Typical veterinary, experimental, or research subjects include monkeys, dogs, cats, rats, mice, rabbits, guinea pigs, horses, and humans.

VII. Antibody Production

In one embodiment, for recombinant production of the antibodies of the present invention, the nucleic acids encoding the two chains are isolated and inserted into one or more replicable vectors for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence. In one embodiment, both the light and heavy chains of the humanized anti-IL-23p19 antibody of the present invention are expressed from the same vector, e.g. a plasmid or an adenoviral vector.

Antibodies of the present invention may be produced by any method known in the art. In one embodiment, antibodies are expressed in mammalian or insect cells in culture, such as chinese hamster ovary (CHO) cells, human embryonic kidney (HEK) 293 cells, mouse myeloma NSO cells, baby hamster kidney (BHK) cells, *Spodoptera frugiperda* ovarian (Sf9) cells. In one embodiment, antibodies secreted from CHO cells are recovered and purified by standard chromatographic methods, such as protein A, cation exchange, anion exchange, hydrophobic interaction, and hydroxyapatite chromatography. Resulting antibodies are concentrated and stored in 20 mM sodium acetate, pH 5.5.

In another embodiment, the antibodies of the present invention are produced in yeast according to the methods described in WO2005/040395. Briefly, vectors encoding the individual light or heavy chains of an antibody of interest are introduced into different yeast haploid cells, e.g. different mating types of the yeast *Pichia pastoris*, which yeast haploid cells are optionally complementary auxotrophs. The transformed haploid yeast cells can then be mated or fused to give a diploid yeast cell capable of producing both the heavy and the light chains. The diploid strain is then able to secret the fully assembled and biologically active antibody. The relative expression levels of the two chains can be optimized, for example, by using vectors with different copy number, using transcriptional promoters of different strengths, or inducing expression from inducible promoters driving transcription of the genes encoding one or both chains.

In one embodiment, the respective heavy and light chains of a plurality of different anti-IL-23p19 antibodies (the "original" antibodies) are introduced into yeast haploid cells to create a library of haploid yeast strains of one mating type expressing a plurality of light chains, and a library of haploid yeast strains of a different mating type expressing a plurality of heavy chains. These libraries of haploid strains can be mated (or fused as spheroplasts) to produce a series of diploid yeast cells expressing a combinatorial library of antibodies comprised of the various possible permutations of light and heavy chains. The combinatorial library of antibodies can then be screened to determine whether any of the antibodies has properties that are superior (e.g. higher affinity for IL-23) to those of the original antibodies. See. e.g., WO2005/040395.

In another embodiment, antibodies of the present invention are human domain antibodies in which portions of an antibody variable domain are linked in a polypeptide of molecular weight approximately 13 kDa. See, e.g., U.S. Pat. Publication No. 2004/0110941. Such single domain, low molecular weight agents provide numerous advantages in terms of ease of synthesis, stability, and route of administration.

VIII. Uses

The present invention provides methods for using engineered anti-IL-23 antibodies and fragments thereof for the treatment and diagnosis of inflammatory disorders and conditions, e.g., of the central nervous system, peripheral nervous system, and gastrointestinal tract, as well as autoimmune and proliferative disorders.

Methods are provided for the treatment of, e.g., multiple sclerosis (MS), including relapsing-remitting MS and primary progressive MS, Alzheimer's disease, amyotrophic lateral sclerosis (a.k.a. ALS; Lou Gehrig's disease), ischemic brain injury, prion diseases, and HIV-associated dementia. Also provided are methods for treating neuropathic pain, posttraumatic neuropathies, Guillain-Barre syndrome (GBS), peripheral polyneuropathy, and nerve regeneration.

Provided are methods for treating or ameliorating one or more of the following features, symptoms, aspects, manifestations, or signs of multiple sclerosis, or other inflammatory disorder or condition of the nervous system: brain lesions, myelin lesions, demyelination, demyelinated plaques, visual disturbance, loss of balance or coordination, spasticity, sensory disturbances, incontinence, pain, weakness, fatigue, paralysis, cognitive impairment, bradyphrenia, diplopia, optic neuritis, paresthesia, gait ataxia, fatigue, Uhtoff's symptom, neuralgia, aphasia, apraxia, seizures, visual-field loss, dementia, extrapyramidal phenomena, depression, sense of well-being, or other emotional symptoms, chronic progressive myelopathy, and a symptom detected by magnetic resonance imaging (MRI), including gadolinium-enhancing lesions, evoked potential recordings, or examination of cerebrospinal fluid. See, e.g., Kenealy et al. (2003) *J. Neuroimmunol.* 143:7-12; Noseworthy et al. (2000) *New Engl. J. Med.* 343:938-952; Miller et al. (2003) *New Engl. J. Med.* 348:15-23; Chang et al. (2002) *New Engl. J. Med.* 346:165-173; Bruck and Stadelmann (2003) *Neurol. Sci.* 24 Suppl. 5:S265-S267.

Moreover, the present invention provides methods for treating and diagnosing inflammatory bowel disorders, e.g., Crohn's disease, ulcerative colitis, celiac disease, and irritable bowel syndrome. Provided are methods for treating or ameliorating one or more of the following symptoms, aspects, manifestations, or signs of an inflammatory bowel disorder: malabsorption of food, altered bowel motility, infection, fever, abdominal pain, diarrhea, rectal bleeding, weight loss, signs of malnutrition, perianal disease, abdominal mass, and growth failure, as well as intestinal complications such as stricture, fistulas, toxic megacolon, perforation, and cancer, and including endoscopic findings, such as, friability, aphthous and linear ulcers, cobblestone appearance, pseudopolyps, and rectal involvement and, in addition, anti-yeast antibodies. See, e.g., Podolsky, supra; Hanauer, supra; Horwitz and Fisher, supra.

Also contemplated is treatment of inflammatory disorders such as psoriasis, atopic dermatitis, arthritis, including rheumatoid arthritis, osteoarthritis, and psoriatic arthritis, autoimmune disorders, such as systemic lupus erythematosus and type I diabetes, and proliferative disorders such as cancer. See, e.g., PCT patent application publications WO 04/081190; WO 04/071517; WO 00/53631; and WO 01/18051.

The IL-23p19 binding compounds of the present invention can also be used in combination with one or more antagonists of other cytokines (e.g. antibodies), including but not limited to, IL-17A, IL-17F, IL-1$\beta$, IL-6 and TGF-$\beta$. See, e.g., Veldhoen (2006) *Immunity* 24:179-189; Dong (2006) *Nat. Rev. Immunol.* 6(4):329-333. In various embodiments, an IL-23p19 binding compound of the invention is administered before, concurrently with, or after administration of the another antagonist or antagonists, such as an anti-IL-17A antibody. In one embodiment, an IL-17A binding compound is used in treatment of the acute early phase of an adverse immune response (e.g. MS, Crohn's Disease) alone or in combination with an IL-23 antagonist antibody of the present invention. In the latter case, the IL-17A binding compound may be gradually decreased and treatment with the antagonist of IL-23 alone is continued to maintain suppression of the adverse response. Alternatively, antagonists to IL-1$\beta$, IL-6 and/or TGF-$\beta$ may be administered concurrently, before or after an IL-23p19 binding compound of the present invention. See Cua and Kastelein (2006) *Nat. Immunol.* 7:557-559; Tato and O'Shea (2006) *Nature* 441:166-168; Iwakura and Ishigame (2006) *J. Clin. Invest.* 116:1218-1222.

The broad scope of this invention is best understood with reference to the following examples, which are not intended to limit the inventions to the specific embodiments. The specific embodiments described herein are offered by way of example only, and the invention is to be limited by the terms of the appended claims, along with the full scope of equivalents to which such claims are entitled.

EXAMPLES

Example 1

General Methods

Standard methods in molecular biology are described. Maniatis et al. (1982) *Molecular Cloning, A Laboratory Manual*, Cold Spring Harbor Laboratory Press, Cold Spring Harbor, N.Y.; Sambrook and Russell (2001) *Molecular Cloning*, 3$^{rd}$ ed., Cold Spring Harbor Laboratory Press, Cold Spring Harbor, N.Y.; Wu (1993) *Recombinant DNA*, Vol. 217, Academic Press, San Diego, Calif. Standard methods also appear in Ausbel et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described. Coligan et al. (2000) *Current Protocols in Protein Science*, Vol. 1, John Wiley and Sons, Inc., New York. Chemical analysis, chemical modification, post-translational modification, production of fusion proteins, glycosylation of proteins are described. See, e.g., Coligan et al. (2000) *Current Protocols in Protein Science*, Vol. 2, John Wiley and Sons, Inc., New York; Ausubel et al. (2001) *Current Protocols in Molecular Biology*, Vol. 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391. Production, purification, and fragmentation of polyclonal and monoclonal antibodies are described. Coligan et al. (2001) *Current Protcols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra. Standard techniques for characterizing ligand/receptor interactions are available. See, e.g., Coligan et al. (2001) *Current Protcols in Immunology*, Vol. 4, John Wiley, Inc., New York.

Methods for flow cytometry, including fluorescence activated cell sorting detection systems (FACS®), are available. See, e.g., Owens et al. (1994) *Flow Cytometry Principles for Clinical Laboratory Practice*, John Wiley and Sons, Hoboken, N.J.; Givan (2001) *Flow Cytometry*, 2$^{nd}$ ed.; Wiley-Liss, Hoboken, N.J.; Shapiro (2003) *Practical Flow Cytometry*, John Wiley and Sons, Hoboken, N.J. Fluorescent reagents suitable for modifying nucleic acids, including nucleic acid primers and probes, polypeptides, and antibodies, for use, e.g., as diagnostic reagents, are available. Molecular Probes (2003) *Catalogue*, Molecular Probes, Inc., Eugene, Oreg.; Sigma-Aldrich (2003) *Catalogue*, St. Louis, Mo.

Standard methods of histology of the immune system are described. See, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, PA; Louis, et al. (2002) *Basic Histology: Text and Atlas*, McGraw-Hill, New York, N.Y.

Software packages and databases for determining, e.g., antigenic fragments, leader sequences, protein folding, functional domains, glycosylation sites, and sequence alignments, are available. See, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne et al. (2000) *Bioinformatics* 16: 741-742; Menne et al. (2000) *Bioinformatics Applications Note* 16:741-742; Wren et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690.

Example 2

Generation and Humanization of Anti-Human IL-23p19 Antibodies

Anti-human IL-23p19 antibodies were generated by immunizing IL-23p19 knockout mice with chimeric IL-23 (human p19:mouse p40). Monoclonal antibodies were prepared by standard methods.

The humanization of the variable domains of murine antibody 13B8 (mouse IgG1/kappa) was performed essentially as described in PCT patent application publications WO 2005/047324 and WO 2005/047326.

Briefly, the amino acid sequence of the non-human VH domain of antibody 13B8 was compared to a group of five human VH germline amino acid sequences; one representative from subgroups IGHV1 and IGHV4 and three representatives from subgroup IGHV3. The VH subgroups are listed in M.-P. Lefranc (2001) "Nomenclature of the Human Immunoglobulin Heavy (IGH) Genes", *Experimental and Clinical Immunogenetics* 18:100-116. Antibody 13B8 scored highest against human heavy chain germline DP-14 in subgroup VH1.

The VL sequence of antibody 13B8 is of the kappa subclass of VL. The amino acid sequence of the non-human VL domain was compared to a group of four human VL kappa germline amino acid sequences. The group of four is comprised of one representative from each of four established human VL subgroups listed in V. Barbie & M.-P. Lefranc (1998) "The Human Immunoglobulin Kappa Variable (IGKV) Genes and Joining (IGKJ) Segments", *Experimental and Clinical Immunogenetics* 15:171-183 and M.-P. Lefranc (2001) "Nomenclature of the Human Immunoglobulin Kappa (IGK) Genes", *Experimental and Clinical Immunogenetics* 18:161-174. The four subgroups also correspond to the four subgroups listed in Kabat et al. (1991-5th Ed.) "Sequences of Proteins of Immunological Interest", U.S. Department of Health and Human Services, NIH Pub. 91-3242, pp. 103-130. Antibody 13B8 scored highest against human light chain germline Z-012 in subgroup VLkI.

Additional amino acid substitutions were made in CDRH2, as discussed supra and disclosed at SEQ ID NOs: 24-26. Humanized 13B8 heavy and light chain variable domains were cloned into vectors encoding a human γ1 (IgG1) heavy chain constant domain and a kappa light chain constant domain, respectively. The resulting humanized 13B8 antibody (IgG1/kappa) binds to human and cynomolgus monkey IL-23 but not to human IL-12, human p40 or mouse IL-23.

Once the target amino acid sequences of the variable heavy and light chains are determined, plasmids encoding the full-length humanized antibody may be generated. Plasmid sequences may be altered using Kunkel mutagenesis (Kunkel (1985) *Proc. Natl. Acad. Sci. U.S.A* 82:488-492) to change the DNA sequence to the target humanized antibody sequences. Simultaneously, codon optimization may be performed to provide for potentially optimal expression.

Humanized forms of other antibodies disclosed herein may be constructed by substituting the human frameworks disclosed for the humanized 13B8 antibody, or by repeating the procedure for selection of the best human frameworks by the methods disclosed in this Example. Substitution of the human frameworks disclosed herein as part of humanized antibody 13B8 is most appropriate for antibodies with CDR sequences similar to 13B8.

Example 3

Determining the Equilibrium Dissociation Constant ($K_d$) for Humanized Anti-Human IL-23 Using KinExA Technology The equilibrium dissociation constant ($K_d$) for anti human IL-23 antibodies is determined using the KinExA 3000 instrument. Sapidyne Instruments Inc., Boise Id., USA KinExA uses the principle of the Kinetic Exclusion Assay method based on measuring the concentration of uncomplexed antibody in a mixture of antibody, antigen and antibody-antigen complex. The concentration of free antibody is measured by exposing the mixture to a solid-phase immobilized antigen for a very brief period of time. In practice, this is accomplished by flowing the solution phase antigen-antibody mixture past antigen-coated particles trapped in a flow cell. Data generated by the instrument are analyzed using custom software. Equilibrium constants are calculated using a mathematical theory based on the following assumptions:

1. The binding follows the reversible binding equation for equilibrium:

$$k_{on}[Ab][Ag]=k_{off}[AbAg]$$

2. Antibody and antigen bind 1:1 and total antibody equals antigen-antibody complex plus free antibody.
3. Instrument signal is linearly related to free antibody concentration.

98 micron PMMA particles (Sapidyne, Cat No. 440198) are coated with biotinylated IL-23 according to Sapidyne "Protocol for coating PMMA particles with biotinylated ligands having short or nonexistent linker arms". In this experiment, biotinylated IL-23 comprises a complex of mouse IL-12p40 and human IL-23p19. EZ-link TFP PEO-biotin (Pierce, Cat. No. 21219) is used to make biotinylated IL-23 according to manufacturer's recommendations (Pierce bulletin 0874). All experimental procedures are done according to the KinExA 3000 manual.

Binding of anti-IL-23p19 antibodies is assessed in a competition binding assay, in which antibodies are pre-incubated with non-linked (native) human IL-23 comprising two disulfide-linked chains, human p19 (SEQ ID NO: 47) and human p40 (GenBank Accession No. P29460), at a series of concentrations. The resulting samples, comprising a mixture of unbound antibodies and IL-23-bound antibodies, are then flowed over the rhIL-23 ("elastikine") PMMA particles described in the preceding paragraph. The amount of antibody captured by the PMMA particles is then detected using a fluorescently labeled secondary antibody.

Table 3 shows the results of the KinExA analysis, including replicate determinations for each antibody.

TABLE 3

$K_d$ Values Determined by KinExA

| Antibody | $K_d$ (pM) |
|---|---|
| m13B8 | 15, 52 |
| hum13B8-a | 64 ± 40, 110, 365, 447 |
| hum13B8-b | 47, 470, 520 |
| hum13B8-c | 47, 52, 470 |

Example 4

Determining the Equilibrium Dissociation Constant ($K_d$) for Humanized Anti-Human IL-23p19 Antibodies Using BIAcore Technology BIAcore determinations are performed essentially as described at Example 4 of commonly assigned U.S. Patent Application Publication No. 2007/0048315. Briefly, ligands (anti-IL-23 mAbs) are immobilized on a BIAcore CM5 sensor chip using standard amine-coupling procedure. IL-23 is diluted in PBS to produce various concentrations. Kinetic constants for the various interactions are determined using BIAevaluation software 3.1. The $K_d$ is determined using the calculated dissociation and association rate constants.

Table 4 provides the $K_d$ values as determined by BIAcore, including replicate determinations.

TABLE 4

$K_d$ Determination by BIAcore

| Antibody | $K_d$ (pM) |
|---|---|
| m13B8 | 173, 228 |
| hum13B8-a | 72-104, 68-100, 81-129 |
| hum13B8-b | 77-129, 69-116 |
| hum13B8-c | 92-153 |

Example 5

Proliferation Bioassays for the Assessment of Neutralizing Anti-IL-23 Antibodies The ability of a monoclonal antibody to biologically neutralize IL-23 was assessed by the application of short-term proliferation bioassays that employ cells that express recombinant IL-23 receptors. The IL-23R transfectant cell line (Ba/F3-2.21o-hIL-23R) expresses both hIL-23R and hIL-12Rβ1, and is responsive to both human IL-23 and cynomolgus monkey IL-23. The transfectant Ba/F3-2.21o cells proliferate in response to human IL-23 and the response can be inhibited by a neutralizing anti-IL-23 antibody. An antibody is titrated against a concentration of IL-23 chosen within the linear region of the dose-response curve, near plateau and above EC50. Proliferation, or lack thereof, is measured by colorimetric means using Alamar Blue, a growth indicator dye based on detection of metabolic activity. The ability of an antibody to neutralize IL-23 is assessed by its IC50 value, or concentration of antibody that induces half-maximal inhibition of IL-23 proliferation.

Ba/F3 transfectants are maintained in RPMI-1640 medium, 10% fetal calf serum, 50 μM 2-mercaptoethanol, 2 mM L-Glutamine, 50 μg/mL penicillin-streptomycin, and 10 ng/mL mouse IL-3. Ba/F3 proliferation bioassays are performed in RPMI-1640 medium, 10% fetal calf serum, 50 μM 2-mercaptoethanol, 2 mM L-Glutamine, and 50 μg/mL penicillin-streptomycin.

Procedure

Assays are performed in 96-well flat bottom plates (Falcon 3072 or similar) in 150 μL per well. Anti-IL-23 antibodies are pre-incubated with IL-23 for 30-60 min, followed by addition of cells and incubation for 40-48 hours. Alamar Blue (Biosource Cat #DAL1100) is added and allowed to develop for 5-12 hours. Absorbance is then read at 570 nm and 600 nm (VERSAmax Microplate Reader, Molecular Probes, Eugene, Oreg., USA), and an $OD_{570-600}$ is obtained.

Cells are used in a healthy growth state, generally at densities of $3-8\times10^5$/mL. Cells are counted, pelleted, washed twice in bioassay medium, and suspended to the appropriate density for plating. An IL-23 dose response is performed using serial 1:3 dilutions (25:50 μL in bioassay medium) of IL-23. An IL-23 concentration of 3 ng/ml (50 pM) is selected for use in antibody assays. A neutralizing antibody dose response is also performed using serial 1:3 dilutions (25:50 μL in bioassay medium).

IC50 values are determined using GraphPad Prism® 3.0 software (Graphpad Software Inc., San Diego, Calif., USA), in which absorbance is plotted against cytokine or antibody concentration and IC50 values are determined using non-linear regression (curve fit) of sigmoidal dose-response.

Table 5 shows the IC50 values for blocking of Ba/F3 cell proliferation by anti-IL-23p19 antibodies. Values for multiple determinations are included for some antibodies.

TABLE 5

| IC50 Values for Blocking of Ba/F3 Cell Proliferation by Anti-IL-23 Antibodies | |
|---|---|
| Antibody | IC50 (pM) |
| m13B8 | 700 |
| hum13B8-a | 1100, 1100 |
| hum13B8-b | 1200, 1100 |
| hum13B8-c | 1100, 2200 |

Example 6

Mouse Splenocyte Assay for IL-23 Based on IL-17 Production

The biological activity of anti-IL-23p19 antibodies of the present invention is assessed using the splenocyte assay essentially as described in Aggarwal et al. (2003) *J. Biol. Chem.* 278:1910 and Stumhofer et al. (2006) *Nature Immunol.* 7:937. The mouse splenocyte assay measures the activity of IL-23 in a sample as a level of IL-17 production by murine splenocytes. The inhibitory activity of anti-IL-23p19 antibodies is then assessed by determining the concentration of antibody necessary to reduce the IL-23 activity in a given sample by 50% (the IC50). The IC50 as measured by this assay is greater than or equal to the equilibrium dissociation binding constant ($K_d$), i.e. the $K_d$ may be equal to or lower than the IC50. As always, lower IC50 and $K_d$ values reflect higher activities and affinities.

Briefly, spleens are obtained from 8-12 wk old female C57BL/6J mice (Jackson Laboratories, Bar Harbor, Me., USA). Spleens are ground, pelleted twice, and filtered through a cell strainer (70 μm nylon). The recovered cells are cultured in 96-well plates ($4\times10^5$ cells/well) in the presence of human IL-23 (10 ng/ml, ~170 pM) and mouse-anti-CD3e antibodies (1 μg/ml) (BD Pharmingen, Franklin Lakes, N.J., USA), with or without the anti-IL-23p19 antibody to be assayed. Anti IL-23p19 antibodies are added at 10 μg/ml and at a series of 3-fold dilutions. Cells are cultured for 72 hours, pelleted, and the supernatant is assayed for IL-17 levels by sandwich ELISA.

IL-17 ELISA is performed as follows. Plates are coated with a capture anti-IL-17 antibody (100 ng/well) overnight at 4° C., washed and blocked. Samples and standards are added and incubated for two hours at room temperature with shaking Plates are washed, and a biotinylated anti-IL-17 detection antibody (100 ng/well) is added and incubated for one hour at room temperature with shaking. The capture and detection antibodies are different antibodies that both bind to mouse IL-17 but do not cross-block. Plates are washed, and bound detection antibody is detected using streptavidin-HRP (horseradish peroxidase) and TMB (3,3',5,5'-tetramethylbenzidine). The plate is then read at 450-650 nm and the concentration of IL-17 in samples is calculated by comparison with standards.

Splenocyte assay IC50 values are provided at Table 6, including some replicate determinations.

TABLE 6

| Splenocyte Assay IC50s | |
|---|---|
| Antibody Clone | IC50 (pM) |
| m13B8 | 28, 54, 64 |
| hum13B8-a | 71-108 |
| hum13B8-b | 110, 221 |
| hum13B8-c | 515 |

Example 7

Characterization of a Preparation of Anti-IL-23p19 Antibody 13B8-b

Humanized anti-IL-23p19 antibody 13B8-b is prepared from mammalian cells using a vector harboring DNA sequences encoding the heavy and light chains of 13B8-b, as provided at SEQ ID NOs: 49 and 50, respectively.

Hum 13B8-b has a $K_d$ of 297 pM for human IL-23 when assayed by BIAcore analysis, essentially as described in Example 4 (supra).

The biological activity of hum13B8-b is assessed using the Ba/F3 proliferation assay, essentially as described in Example 5 (supra), except that 340 pM of IL-23 is used to stimulate proliferation, rather than 50 pM. The inhibitory activity of anti-IL-23p19 antibodies (the IC50) is assessed by determining the concentration of antibody necessary to reduce the IL-23 activity in a given sample by 50%. As always, lower IC50 values reflect higher activities. Hum13B8-b exhibits an IC50 of 187 pM in the Ba/F3 proliferation assay.

The biological activity of hum13B8-b is also assessed using a human splenocyte assay, essentially as described in Example 6 (supra) with the exception that splenocytes are obtained from human spleens rather than mouse, no anti-CD3e antibody is used, and that IFN-γ is the readout rather than IL-17. The assay measures the activity of IL-23 in a sample by determining the level of IFN-γ production by human primary splenocytes. Human splenocytes are exposed to human IL-23 (170 pM) in the presence of various concentrations of anti-IL-23p19 antibody hum13B8-b, or in the absence of the antibody. IFN-γ is detected by sandwich ELISA. Hum13B8-b exhibits an IC50 of 59-144 pM in the human splenocyte assay.

The biological activity of hum13B8-b is further assessed using a KIT225 STAT-3 phosphorylation assay, essentially as described in Parham et al. (2002) *J. Immunol.* 168:5699. Human KIT225 cells, a leukemic T cell line, are stimulated with 138 µM human IL-23 in the presence of various concentrations of anti-IL-23p19 antibody hum13B8-b, or in the absence of the antibody. IL-23 activity is measured by detecting the level of STAT3 phosphorylation. Hum13B8-b exhibits an IC50 of 130 pM in the KIT225 assay.

Example 8

Epitope for Humanized Anti-IL-23p19 Antibody 13B8-b

The epitope for the binding of humanized antibody 13B8-b to human IL-23p19 (SEQ ID NO: 47) was determined by X-ray crystallography. Coordinates were determined for a complex of a Fab fragment of the humanized anti-IL-23p19 antibody 13B8-b and non-linked human IL-23, which comprises p19 and p40 subunits. The p40 subunit in the IL-23 used to determine the crystal structure has a N222Q substitution in which Asn222 is replaced by Gln. The sequence of human IL-23p19 is found at SEQ ID NO: 47 and the sequence of the mature form of human IL-12/IL-23 p40 is found at residues 23-328 of GenBank Accession No. P29460. The humanized anti-IL-23p19 antibody 13B8-b comprises the humanized 13B8-b heavy chain (SEQ ID NO: 7) humanized 13B8-b light chain (SEQ ID NO: 14). Crystallization conditions are 15% polyethylene glycol 4000, 60 mM sodium acetate, 100 mM TRIS-HCl (pH 8). Crystals may also be obtained with other buffers at or around pH 8.

IL-23 amino acid residues within 4.0 Å of residues on antibody 13B8-b include K20, T23, W26, S27, P30, E82, S95, L96, L97, P98, D99, P101, G103, Q104, H106, A107 and L110. Additional residues L24, L85, T91, S100 and V102 were within 5.0 Å. An amino acid residue on IL-23p19 is considered to be within a given distance of the antibody (e.g. 4.0 Å or 5.0 Å) if the coordinates of any atom of the residue are within the given distance of the coordinates of any atom of the antibody.

Most of these contacted residues fall into two main clusters along the primary structure of IL-23p19, with the first cluster comprising residues 20-30 (in which 6 of 11 residues are within 5.0 Å of the antibody and 5 of 11 are within 4.0 Å) and the second cluster comprising residues 82-110 (in which 16 of 29 residues are within 5.0 Å of the antibody and 12 of 29 are within 4.0 Å). These clusters define epitopes comprising stretches of 11 or more contiguous amino acid residues of IL-23p19 in which 30%, 40%, 45%, 50% or 54% or more of the residues are within 4.0 Å or 5.0 Å of the antibody.

Antibodies binding to either or both of these clusters would be expected to block binding of antibody 13B8-b, and would be expected to exhibit similar biological activities.

Table 7 provides a brief description of the sequences in the sequence listing.

TABLE 7

| SEQ ID NO: | Description |
|---|---|
| 1 | m1A11 $V_H$ |
| 2 | m11C1 $V_H$ |
| 3 | m5F5 $V_H$ |
| 4 | m21D1 $V_H$ |
| 5 | m13B8 $V_H$ |
| 6 | hum13B8 HC-a |
| 7 | hum13B8 HC-b |
| 8 | hum13B8 HC-c |
| 9 | m1A11 $V_L$ |
| 10 | m11C1 $V_L$ |
| 11 | m5F5 $V_L$ |
| 12 | m21D1 $V_L$ |
| 13 | m13B8 $V_L$ |
| 14 | hum13B8 LC |
| 15 | m1A11 CDRH1 |
| 16 | m11C1 CDRH1 |
| 17 | m5F5 CDRH1 |
| 18 | m21D1 CDRH1 |
| 19 | m13B8 CDRH1 |
| 20 | m1A11 CDRH2 |
| 21 | m11C1 CDRH2 |
| 22 | m5F5 CDRH2 |
| 23 | m21D1 CDRH2 |
| 24 | m13B8 CDRH2-a |
| 25 | h13B8 CDRH2-b |
| 26 | h13B8 CDRH2-c |
| 27 | m1A11 CDRH3 |
| 28 | m11C1 CDRH3 |
| 29 | m5F5 CDRH3 |
| 30 | m21D1 CDRH3 |
| 31 | m13B8 CDRH3 |
| 32 | m1A11 CDRL1 |
| 33 | m11C1 CDRL1 |
| 34 | m5F5 CDRL1 |
| 35 | m21D1 CDRL1 |
| 36 | m13B8 CDRL1 |
| 37 | m1A11 CDRL2 |
| 38 | m11C1 CDRL2 |
| 39 | m5F5 CDRL2 |
| 40 | m21D1 CDRL2 |
| 41 | m13B8 CDRL2 |
| 42 | m1A11 CDRL3 |
| 43 | m11C1 CDRL3 |
| 44 | m5F5 CDRL3 |
| 45 | m21D1 CDRL3 |
| 46 | m13B8 CDRL3 |
| 47 | human IL-23p19 |
| 48 | mouse IL-23p19 |
| 49 | hum13B8-b HC DNA |
| 50 | hum13B8 LC DNA |

What is claimed is:

1. A purified binding compound that binds to human IL-23, comprising:
   a) an antibody light chain variable domain, or antigen binding fragment thereof, comprising CDRL1, CDRL2 and CDRL3, wherein:
   CDRL1 comprises the sequence of SEQ ID NO: 36;
   CDRL2 comprises the sequence of SEQ ID NO: 41; and
   CDRL3 comprises the sequence of SEQ ID NO: 46; and
   b) an antibody heavy chain variable domain, or antigen binding fragment thereof, comprising CDRH1, CDRH2 and CDRH3, wherein:
   CDRH1 comprises the sequence of SEQ ID NO: 19;
   CDRH2 comprises a sequence selected from the group consisting of SEQ ID NOs: 24-26; and
   CDRH3 comprises the sequence of SEQ ID NO: 31.

2. The binding compound of claim 1 wherein CDRL2 comprises the sequence of SEQ ID NO: 24.

3. The binding compound of claim 1 wherein CDRL2 comprises the sequence of SEQ ID NO: 25.

4. The binding compound of claim 1 wherein CDRL2 comprises the sequence of SEQ ID NO: 26.

5. The binding compound of claim 2 comprising:
   a) an antibody light chain variable domain comprising residues 1-108 of SEQ ID NO: 14; and
   b) an antibody heavy chain variable domain comprising residues 1-116 of SEQ ID NO: 6.

6. The binding compound of claim 3 comprising:
   a) an antibody light chain variable domain comprising residues 1-108 of SEQ ID NO: 14; and
   b) an antibody heavy chain variable domain comprising residues 1-116 of SEQ ID NO: 7.

7. The binding compound of claim 4 comprising:
   a) an antibody light chain variable domain comprising residues 1-108 of SEQ ID NO: 14; and
   b) an antibody heavy chain variable domain comprising residues 1-116 of SEQ ID NO: 8.

8. The binding compound of claim 5 comprising an antibody light chain and an antibody heavy chain, wherein:
   a) the antibody light chain comprises the sequence of SEQ ID NO: 14; and
   b) the antibody heavy chain comprises the sequence of SEQ ID NO: 6.

9. The binding compound of claim 6 comprising an antibody light chain and an antibody heavy chain, wherein:
   a) the antibody light chain comprises the sequence of SEQ ID NO: 14; and
   b) the antibody heavy chain comprises the sequence of SEQ ID NO: 7.

10. The binding compound of claim 7 comprising an antibody light chain and an antibody heavy chain, wherein:
    a) the antibody light chain comprises the sequence of SEQ ID NO: 14; and
    b) the antibody heavy chain comprises the sequence of SEQ ID NO: 8.

11. The binding compound of claim 1, further comprising a heavy chain constant region comprising a γ1 human heavy chain constant region.

12. The binding compound of claim 1, further comprising a heavy chain constant region comprising a γ4 human heavy chain constant region.

13. The binding compound of claim 2, wherein the binding compound is an antibody fragment selected from the group consisting of Fab, Fab', Fab'-SH, Fv, scFv, $F(ab')_2$, and a diabody.

14. The binding compound of claim 3, wherein the binding compound is an antibody fragment selected from the group consisting of Fab, Fab', Fab'-SH, Fv, scFv, $F(ab')_2$, and a diabody.

15. The binding compound of claim 4, wherein the binding compound is an antibody fragment selected from the group consisting of Fab, Fab', Fab'-SH, Fv, scFv, $F(ab')_2$, and a diabody.

16. The binding compound of claim 5, wherein the binding compound is an antibody fragment selected from the group consisting of Fab, Fab', Fab'-SH, Fv, scFv, $F(ab')_2$, and a diabody.

17. The binding compound of claim 6, wherein the binding compound is an antibody fragment selected from the group consisting of Fab, Fab', Fab'-SH, Fv, scFv, $F(ab')_2$, and a diabody.

18. The binding compound of claim 7, wherein the binding compound is an antibody fragment selected from the group consisting of Fab, Fab', Fab'-SH, Fv, scFv, $F(ab')_2$, and a diabody.

19. A pharmaceutical composition comprising the binding compound of claim 2 in combination with a pharmaceutically acceptable carrier or diluent.

20. A pharmaceutical composition comprising the binding compound of claim 3 in combination with a pharmaceutically acceptable carrier or diluent.

21. A pharmaceutical composition comprising the binding compound of claim 4 in combination with a pharmaceutically acceptable carrier or diluent.

22. A pharmaceutical composition comprising the binding compound of claim 5 in combination with a pharmaceutically acceptable carrier or diluent.

23. A pharmaceutical composition comprising the binding compound of claim 6 in combination with a pharmaceutically acceptable carrier or diluent.

24. A pharmaceutical composition comprising the binding compound of claim 7 in combination with a pharmaceutically acceptable carrier or diluent.

25. A pharmaceutical composition comprising the binding compound of claim 8 in combination with a pharmaceutically acceptable carrier or diluent.

26. A pharmaceutical composition comprising the binding compound of claim 9 in combination with a pharmaceutically acceptable carrier or diluent.

27. A pharmaceutical composition comprising the binding compound of claim 10 in combination with a pharmaceutically acceptable carrier or diluent.

* * * * *

UNITED STATES PATENT AND TRADEMARK OFFICE
CERTIFICATE OF CORRECTION

PATENT NO. : 8,404,813 B2
APPLICATION NO. : 13/031544
DATED : March 26, 2013
INVENTOR(S) : Presta Page 1 of 1

It is certified that error appears in the above-identified patent and that said Letters Patent is hereby corrected as shown below:

In the Claims

In Claim 2, Column 67, Line 17, the text reading "The method of claim 1, wherein CDRL2" should read -- The method of claim 1, wherein CDRH2 --.

In Claim 3, Column 67, Line 19, the text reading "The method of claim 1, wherein CDRL2" should read -- The method of claim 1, wherein CDRH2 --.

In Claim 4, Column 67, Line 21, the text reading "The method of claim 1, wherein CDRL2" should read -- The method of claim 1, wherein CDRH2 --.

Signed and Sealed this
Twenty-fifth Day of December, 2018

Andrei Iancu
*Director of the United States Patent and Trademark Office*

UNITED STATES PATENT AND TRADEMARK OFFICE

(12)            CERTIFICATE EXTENDING PATENT TERM
UNDER 35 U.S.C. § 156

| | | | |
|---|---|---|---|
| (68) | PATENT NO. | : | 8,404,813 |
| (45) | ISSUED | : | March 26, 2013 |
| (75) | INVENTOR | : | Leonard G. Presta |
| (73) | PATENT OWNER | : | Merck Sharp & Dohme Corp. |
| (95) | PRODUCT | : | ILUMYA® (Tildrakizumab-asmn) |

This is to certify that an application under 35 U.S.C. § 156 has been filed in the United States Patent and Trademark Office, requesting extension of the term of U.S. Patent No. 8,404,813 based upon the regulatory review of the product ILUMYA® (Tildrakizumab-asmn) by the Food and Drug Administration. According to United States Patent and Trademark Office records, the original expiration date of the patent as of the date of issuance of this certificate is February 21, 2028. Because it appears that the requirements of the law have been met, this certificate extends the term of the patent for the period of

(94)                           1,092 days subject to the payment of maintenance fees as provided by law, with all rights pertaining thereto as provided by 35 U.S.C. § 156.

I have caused the seal of the United States Patent and Trademark Office to be affixed this 14th day of October 2021.

Drew Hirshfeld
Commissioner for Patents, Performing the Functions and Duties of the Under Secretary of Commerce for Intellectual Property and Director of the United States Patent and Trademark Office

SEQUENCE LISTING

<160> NUMBER OF SEQ ID NOS: 50

<210> SEQ ID NO 1
<211> LENGTH: 117
<212> TYPE: PRT
<213> ORGANISM: Mus musculus -continued

<400> SEQUENCE: 1

```
Glu Val Gln Leu Gln Gln Ser Gly Pro Glu Leu Val Lys Thr Gly Ala
 1               5                  10                  15
Ser Val Asn Ile Ser Cys Lys Ala Ser Gly Tyr Ser Phe Thr Ala Tyr
             20                  25                  30
Tyr Ile Gln Trp Val Lys Gln Ser Arg Gly Lys Ser Leu Glu Trp Ile
         35                  40                  45
Gly Tyr Ile Ser Cys Tyr Asn Gly Ala Thr Arg Tyr Asn Gln Lys Phe
     50                  55                  60
Lys Gly Lys Ala Thr Phe Thr Val Asp Thr Ser Ser Thr Ala Tyr
 65                  70                  75                  80
Met Gln Phe Ser Ser Leu Thr Ser Glu Asp Ser Ala Val Tyr Phe Cys
                 85                  90                  95
Ala Arg Gln Gly Phe Tyr Ala Met Asp Tyr Trp Gly Gln Gly Thr Ser
            100                 105                 110
Val Thr Val Ser Ser
        115
```

<210> SEQ ID NO 2
<211> LENGTH: 116
<212> TYPE: PRT
<213> ORGANISM: Mus musculus

<400> SEQUENCE: 2

```
His Val Gln Leu Gln Gln Ser Gly Pro Glu Val Val Arg Pro Gly Ala
 1               5                  10                  15
Ser Val Lys Leu Ser Cys Lys Ala Ser Gly Tyr Ile Phe Ser Ala Tyr
             20                  25                  30
Trp Met Thr Trp Val Lys Gln Arg Pro Gly Gln Gly Leu Glu Trp Ile
         35                  40                  45
Gly Gln Ile Phe Pro Val Arg Gly Ser Ala Asp Tyr Asn Glu Ile Phe
     50                  55                  60
Glu Gly Lys Ala Thr Leu Thr Val Asp Thr Ser Ser Ser Thr Ala Tyr
 65                  70                  75                  80
Ile Gln Leu Ser Ser Leu Thr Ser Glu Asp Ser Ala Val Tyr Tyr Cys
                 85                  90                  95
Ala Arg Gly Gly Gly Phe Ala Tyr Trp Gly Gln Gly Thr Leu Val
            100                 105                 110
Thr Val Ser Ala
        115
```

<210> SEQ ID NO 3
<211> LENGTH: 124
<212> TYPE: PRT
<213> ORGANISM: Mus musculus

<400> SEQUENCE: 3

```
Gln Val Gln Leu Gln Gln Ser Gly Ala Glu Leu Ala Arg Pro Gly Ala
 1               5                  10                  15
Ser Val Lys Leu Ser Cys Lys Ala Ser Gly Tyr Thr Phe Thr Ser Tyr
             20                  25                  30
Gly Ile Ser Trp Val Lys Gln Arg Thr Gly Gln Asp Leu Glu Trp Ile
         35                  40                  45
Gly Glu Ile Tyr Pro Arg Ser Val Asn Ser Tyr Tyr Asn Glu Arg Phe
     50                  55                  60
Lys Gly Lys Ala Thr Leu Thr Ala Asp Lys Ser Ser Ser Thr Ala Tyr
```

Met Glu Leu Arg Ser Leu Thr Ser Glu Asp Ser Ala Val Tyr Phe Cys
     65                  70                  75                  80

Ala Arg Gly Gly Asn Tyr Tyr Gly Arg Asn Tyr Gly Asp Tyr Phe Asp
             85                  90                  95

Tyr Trp Gly Gln Gly Thr Thr Leu Thr Val Ser Ser
            115                 120

<210> SEQ ID NO 4
<211> LENGTH: 116
<212> TYPE: PRT
<213> ORGANISM: Mus musculus

<400> SEQUENCE: 4

Gln Val Gln Leu Gln Gln Ser Gly Leu Glu Leu Val Lys Pro Gly Ser
  1               5                  10                  15

Ser Leu Lys Ile Ser Cys Lys Ala Ser Gly Tyr Ser Phe Thr Ser Phe
             20                  25                  30

Phe Ile His Trp Leu Lys Gln Arg Pro Gly Gln Gly Leu Glu Trp Ile
         35                  40                  45

Gly Trp Ile Phe Pro Gly Asn His Asp Val Glu Tyr Asn Glu Lys Phe
     50                  55                  60

Lys Gly Lys Ala Thr Leu Thr Ala Asp Thr Ser Ser Ser Thr Ala Asp
 65                  70                  75                  80

Met His Leu Ser Ser Leu Thr Ser Glu Asp Ser Ala Val Tyr Phe Cys
             85                  90                  95

Ala Arg Gly Gly Gly Asn Leu Pro Tyr Trp Gly Gln Gly Thr Leu Val
            100                 105                 110

Thr Val Ser Ala
        115

<210> SEQ ID NO 5
<211> LENGTH: 116
<212> TYPE: PRT
<213> ORGANISM: Mus musculus

<400> SEQUENCE: 5

His Val Gln Leu Gln Gln Ser Gly Pro Glu Leu Val Arg Pro Gly Ala
  1               5                  10                  15

Ser Val Glu Leu Ser Cys Lys Ala Ser Gly Tyr Ile Phe Ile Thr Tyr
             20                  25                  30

Trp Met Thr Trp Met Lys Gln Arg Pro Gly Gln Gly Leu Glu Trp Ile
         35                  40                  45

Gly Gln Ile Phe Pro Ala Ser Gly Ser Ala Asp Tyr Asn Glu Met Phe
     50                  55                  60

Glu Gly Lys Ala Thr Leu Thr Val Asp Thr Ser Ser Asn Thr Ala Tyr
 65                  70                  75                  80

Met Gln Leu Ser Ser Leu Thr Ser Glu Asp Ser Ala Val Tyr Phe Cys
             85                  90                  95

Ala Arg Gly Gly Gly Gly Phe Ala Tyr Trp Gly Gln Gly Thr Leu Val
            100                 105                 110

Thr Val Ser Ala
        115

<210> SEQ ID NO 6
<211> LENGTH: 446
<212> TYPE: PRT
<213> ORGANISM: Artificial Sequence

```
<220> FEATURE:
<223> OTHER INFORMATION: Human frameworks, rodent CDRs
<220> FEATURE:
<221> NAME/KEY: DOMAIN
<222> LOCATION: (1)..(116)
<223> OTHER INFORMATION: Variable Domain

<400> SEQUENCE: 6
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ile Thr Tyr
            20                  25                  30

Trp Met Thr Trp Val Arg Gln Ala Pro Gly Gln Gly Leu Glu Trp Met
        35                  40                  45

Gly Gln Ile Phe Pro Ala Ser Gly Ser Ala Asp Tyr Asn Glu Met Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Gly Gly Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

```
Gln Pro Glu Asn Asn Tyr Lys Thr Thr Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 7
<211> LENGTH: 446
<212> TYPE: PRT
<213> ORGANISM: Artificial Sequence
<220> FEATURE:
<223> OTHER INFORMATION: Human frameworks, rodent CDRs
<220> FEATURE:
<221> NAME/KEY: DOMAIN
<222> LOCATION: (1)..(116)
<223> OTHER INFORMATION: Variable Domain

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ile Thr Tyr
            20                  25                  30

Trp Met Thr Trp Val Arg Gln Ala Pro Gly Gln Gly Leu Glu Trp Met
        35                  40                  45

Gly Gln Ile Phe Pro Ala Ser Gly Ser Ala Asp Tyr Asn Glu Lys Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Gly Phe Ala Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
            210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285
```

-continued

```
Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Asp Glu Leu Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
    435                 440                 445

<210> SEQ ID NO 8
<211> LENGTH: 446
<212> TYPE: PRT
<213> ORGANISM: Artificial Sequence
<220> FEATURE:
<223> OTHER INFORMATION: Human frameworks, rodent CDRs
<220> FEATURE:
<221> NAME/KEY: DOMAIN
<222> LOCATION: (1)..(116)
<223> OTHER INFORMATION: Variable Domain

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ile Thr Tyr
            20                  25                  30

Trp Met Thr Trp Val Arg Gln Ala Pro Gly Gln Gly Leu Glu Trp Met
        35                  40                  45

Gly Gln Ile Phe Pro Ala Ser Gly Ser Ala Asp Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Gly Gly Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190
```

```
Gly Thr Gln Thr Tyr Ile Cys Asn Val Asn His Lys Pro Ser Asn Thr
            195                 200                 205
Lys Val Asp Lys Lys Val Glu Pro Lys Ser Cys Asp Lys Thr His Thr
    210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
    275                 280                 285
Lys Pro Arg Glu Glu Gln Tyr Asn Ser Thr Tyr Arg Val Val Ser Val
290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
    355                 360                 365
Lys Gly Phe Tyr Pro Ser Asp Ile Ala Val Glu Trp Glu Ser Asn Gly
370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
    435                 440                 445

<210> SEQ ID NO 9
<211> LENGTH: 113
<212> TYPE: PRT
<213> ORGANISM: Mus musculus

<400> SEQUENCE: 9

Asn Val Val Met Thr Gln Thr Pro Leu Thr Leu Ser Val Thr Ile Gly
1               5                   10                  15
Gln Pro Ala Ser Ile Ser Cys Lys Ser Ser Gln Ser Leu Leu Asp Ser
            20                  25                  30
Asp Gly Lys Thr Tyr Leu Asn Trp Leu Leu Gln Arg Pro Gly Gln Ser
        35                  40                  45
Pro Lys Arg Leu Ile Tyr Leu Val Ser Lys Leu Asp Ser Gly Val Pro
    50                  55                  60
Asp Arg Phe Thr Gly Ser Gly Ser Gly Thr Asp Phe Thr Leu Lys Ile
65                  70                  75                  80
Ser Arg Val Glu Ala Glu Asp Leu Gly Leu Tyr Tyr Cys Trp Gln Gly
                85                  90                  95
Thr His Phe Pro Phe Thr Phe Gly Ser Gly Thr Lys Leu Glu Ile Lys
            100                 105                 110
Arg
```

<210> SEQ ID NO 10
<211> LENGTH: 108
<212> TYPE: PRT
<213> ORGANISM: Mus musculus

<400> SEQUENCE: 10

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Glu Lys Trp Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Ser
65                  70                  75                  80

Glu Asp Phe Gly Ser Tyr Tyr Cys Gln His Tyr Gly Thr Pro Phe
                85                  90                  95

Thr Phe Gly Ser Gly Thr Lys Leu Glu Ile Lys Arg
            100                 105

<210> SEQ ID NO 11
<211> LENGTH: 111
<212> TYPE: PRT
<213> ORGANISM: Mus musculus

<400> SEQUENCE: 11

Ser Gln Ala Val Val Thr Gln Glu Ser Ala Leu Thr Thr Ser Pro Gly
1               5                   10                  15

Glu Thr Val Thr Leu Thr Cys Arg Ser Ser Thr Gly Ala Val Ile Thr
            20                  25                  30

Ser Asn Asp Ala Asn Trp Val Gln Glu Lys Pro Asp His Ser Phe Thr
        35                  40                  45

Gly Leu Ile Gly Gly Thr Asn Asn Arg Ala Pro Gly Val Pro Ala Arg
    50                  55                  60

Phe Ser Gly Ser Leu Ile Gly Asp Lys Ala Ala Leu Thr Ile Thr Gly
65                  70                  75                  80

Ala Gln Thr Glu Asp Glu Ala Ile Tyr Phe Cys Ala Leu Trp Tyr Ser
                85                  90                  95

Asn His Trp Val Phe Gly Gly Gly Thr Lys Leu Thr Val Leu Gly
            100                 105                 110

<210> SEQ ID NO 12
<211> LENGTH: 108
<212> TYPE: PRT
<213> ORGANISM: Mus musculus

<400> SEQUENCE: 12

Asp Ile Gln Met Thr Gln Ser Pro Val Ser Leu Ser Ala Ser Val Gly
1               5                   10                  15

Glu Thr Val Thr Ile Thr Cys Arg Ala Ser Glu Asn Val Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Phe Gly Thr Pro Leu
                85                  90                  95

Thr Phe Gly Ala Gly Thr Lys Leu Asp Leu Lys Arg
                100                 105

<210> SEQ ID NO 13
<211> LENGTH: 108
<212> TYPE: PRT
<213> ORGANISM: Mus musculus

<400> SEQUENCE: 13

Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Ile Tyr Ser Tyr
                20                  25                  30

Leu Ala Trp Tyr Gln Gln Lys Gln Gly Lys Ser Pro Gln Leu Leu Val
            35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Arg Leu Gln Pro
65                  70                  75                  80

Glu Asp Phe Gly Arg Tyr Phe Cys Gln His His Tyr Gly Ile Pro Phe
                85                  90                  95

Thr Phe Gly Ser Gly Thr Lys Leu Glu Ile Lys Arg
                100                 105

<210> SEQ ID NO 14
<211> LENGTH: 214
<212> TYPE: PRT
<213> ORGANISM: Artificial Sequence
<220> FEATURE:
<223> OTHER INFORMATION: Human frameworks, rodent CDRs
<220> FEATURE:
<221> NAME/KEY: DOMAIN
<222> LOCATION: (1)..(108)
<223> OTHER INFORMATION: Variable Domain

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Ser Tyr
                20                  25                  30

Leu Ala Trp Tyr Gln Gln Lys Pro Gly Lys Ala Pro Lys Leu Leu Ile
            35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Ile Pro Phe
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 15
<211> LENGTH: 10
<212> TYPE: PRT
<213> ORGANISM: Mus musculus

<400> SEQUENCE: 15

Gly Tyr Ser Phe Thr Ala Tyr Tyr Ile Gln
1               5                   10

<210> SEQ ID NO 16
<211> LENGTH: 10
<212> TYPE: PRT
<213> ORGANISM: Mus musculus

<400> SEQUENCE: 16

Gly Tyr Ile Phe Ser Ala Tyr Trp Met Thr
1               5                   10

<210> SEQ ID NO 17
<211> LENGTH: 10
<212> TYPE: PRT
<213> ORGANISM: Mus musculus

<400> SEQUENCE: 17

Gly Tyr Thr Phe Thr Ser Tyr Gly Ile Ser
1               5                   10

<210> SEQ ID NO 18
<211> LENGTH: 10
<212> TYPE: PRT
<213> ORGANISM: Mus musculus

<400> SEQUENCE: 18

Gly Tyr Ser Phe Thr Ser Phe Phe Ile His
1               5                   10

<210> SEQ ID NO 19
<211> LENGTH: 10
<212> TYPE: PRT
<213> ORGANISM: Mus musculus

<400> SEQUENCE: 19

Gly Tyr Ile Phe Ile Thr Tyr Trp Met Thr
1               5                   10

<210> SEQ ID NO 20
<211> LENGTH: 17
<212> TYPE: PRT
<213> ORGANISM: Mus musculus

<400> SEQUENCE: 20

Tyr Ile Ser Cys Tyr Asn Gly Ala Thr Arg Tyr Asn Gln Lys Phe Lys
1               5                   10                  15

Gly
```

```
<210> SEQ ID NO 21
<211> LENGTH: 17
<212> TYPE: PRT
<213> ORGANISM: Mus musculus

<400> SEQUENCE: 21

Gln Ile Phe Pro Val Arg Gly Ser Ala Asp Tyr Asn Glu Ile Phe Glu
1               5                   10                  15

Gly

<210> SEQ ID NO 22
<211> LENGTH: 17
<212> TYPE: PRT
<213> ORGANISM: Mus musculus

<400> SEQUENCE: 22

Glu Ile Tyr Pro Arg Ser Val Asn Ser Tyr Tyr Asn Glu Arg Phe Lys
1               5                   10                  15

Gly

<210> SEQ ID NO 23
<211> LENGTH: 17
<212> TYPE: PRT
<213> ORGANISM: Mus musculus

<400> SEQUENCE: 23

Trp Ile Phe Pro Gly Asn His Asp Val Glu Tyr Asn Glu Lys Phe Lys
1               5                   10                  15

Gly

<210> SEQ ID NO 24
<211> LENGTH: 17
<212> TYPE: PRT
<213> ORGANISM: Mus musculus

<400> SEQUENCE: 24

Gln Ile Phe Pro Ala Ser Gly Ser Ala Asp Tyr Asn Glu Met Phe Glu
1               5                   10                  15

Gly

<210> SEQ ID NO 25
<211> LENGTH: 17
<212> TYPE: PRT
<213> ORGANISM: Artificial Sequence
<220> FEATURE:
<223> OTHER INFORMATION: Rodent CDR with one amino acid substitution

<400> SEQUENCE: 25

Gln Ile Phe Pro Ala Ser Gly Ser Ala Asp Tyr Asn Glu Lys Phe Glu
1               5                   10                  15

Gly

<210> SEQ ID NO 26
<211> LENGTH: 17
<212> TYPE: PRT
<213> ORGANISM: Artificial Sequence
<220> FEATURE:
<223> OTHER INFORMATION: Rodent CDR with four amino acid substitutions

<400> SEQUENCE: 26

Gln Ile Phe Pro Ala Ser Gly Ser Ala Asp Tyr Ala Gln Lys Leu Gln
1               5                   10                  15
```

Gly

```
<210> SEQ ID NO 27
<211> LENGTH: 8
<212> TYPE: PRT
<213> ORGANISM: Mus musculus

<400> SEQUENCE: 27

Gln Gly Phe Tyr Ala Met Asp Tyr
1               5

<210> SEQ ID NO 28
<211> LENGTH: 7
<212> TYPE: PRT
<213> ORGANISM: Mus musculus

<400> SEQUENCE: 28

Gly Gly Gly Gly Phe Ala Tyr
1               5

<210> SEQ ID NO 29
<211> LENGTH: 15
<212> TYPE: PRT
<213> ORGANISM: Mus musculus

<400> SEQUENCE: 29

Gly Gly Asn Tyr Tyr Gly Arg Asn Tyr Gly Asp Tyr Phe Asp Tyr
1               5                   10                  15

<210> SEQ ID NO 30
<211> LENGTH: 7
<212> TYPE: PRT
<213> ORGANISM: Mus musculus

<400> SEQUENCE: 30

Gly Gly Gly Asn Leu Pro Tyr
1               5

<210> SEQ ID NO 31
<211> LENGTH: 7
<212> TYPE: PRT
<213> ORGANISM: Mus musculus

<400> SEQUENCE: 31

Gly Gly Gly Gly Phe Ala Tyr
1               5

<210> SEQ ID NO 32
<211> LENGTH: 16
<212> TYPE: PRT
<213> ORGANISM: Mus musculus

<400> SEQUENCE: 32

Lys Ser Ser Gln Ser Leu Leu Asp Ser Asp Gly Lys Thr Tyr Leu Asn
1               5                   10                  15

<210> SEQ ID NO 33
<211> LENGTH: 11
<212> TYPE: PRT
<213> ORGANISM: Mus musculus

<400> SEQUENCE: 33

Arg Ala Ser Glu Asn Ile Tyr Ser Tyr Leu Ala
1               5                   10
```

```
<210> SEQ ID NO 34
<211> LENGTH: 14
<212> TYPE: PRT
<213> ORGANISM: Mus musculus

<400> SEQUENCE: 34

Arg Ser Ser Thr Gly Ala Val Ile Thr Ser Asn Asp Ala Asn
1               5                   10

<210> SEQ ID NO 35
<211> LENGTH: 11
<212> TYPE: PRT
<213> ORGANISM: Mus musculus

<400> SEQUENCE: 35

Arg Thr Ser Glu Asn Ile Tyr Ser Tyr Leu Ala
1               5                   10

<210> SEQ ID NO 36
<211> LENGTH: 11
<212> TYPE: PRT
<213> ORGANISM: Mus musculus

<400> SEQUENCE: 36

Arg Thr Ser Glu Asn Ile Tyr Ser Tyr Leu Ala
1               5                   10

<210> SEQ ID NO 37
<211> LENGTH: 7
<212> TYPE: PRT
<213> ORGANISM: Mus musculus

<400> SEQUENCE: 37

Leu Val Ser Lys Leu Asp Ser
1               5

<210> SEQ ID NO 38
<211> LENGTH: 7
<212> TYPE: PRT
<213> ORGANISM: Mus musculus

<400> SEQUENCE: 38

Asn Ala Lys Thr Leu Ala Glu
1               5

<210> SEQ ID NO 39
<211> LENGTH: 7
<212> TYPE: PRT
<213> ORGANISM: Mus musculus

<400> SEQUENCE: 39

Gly Thr Asn Asn Arg Ala Pro
1               5

<210> SEQ ID NO 40
<211> LENGTH: 7
<212> TYPE: PRT
<213> ORGANISM: Mus musculus

<400> SEQUENCE: 40

Asn Ala Lys Thr Leu Ala Glu
1               5

<210> SEQ ID NO 41
<211> LENGTH: 7
<212> TYPE: PRT
```

<213> ORGANISM: Mus musculus

<400> SEQUENCE: 41

Asn Ala Lys Thr Leu Ala Glu
1               5

<210> SEQ ID NO 42
<211> LENGTH: 9
<212> TYPE: PRT
<213> ORGANISM: Mus musculus

<400> SEQUENCE: 42

Trp Gln Gly Thr His Phe Pro Phe Thr
1               5

<210> SEQ ID NO 43
<211> LENGTH: 9
<212> TYPE: PRT
<213> ORGANISM: Mus musculus

<400> SEQUENCE: 43

Gln His His Tyr Gly Thr Pro Phe Thr
1               5

<210> SEQ ID NO 44
<211> LENGTH: 9
<212> TYPE: PRT
<213> ORGANISM: Mus musculus

<400> SEQUENCE: 44

Ala Leu Trp Tyr Ser Asn His Trp Val
1               5

<210> SEQ ID NO 45
<211> LENGTH: 9
<212> TYPE: PRT
<213> ORGANISM: Mus musculus

<400> SEQUENCE: 45

Gln His His Tyr Gly Ile Pro Phe Thr
1               5

<210> SEQ ID NO 46
<211> LENGTH: 9
<212> TYPE: PRT
<213> ORGANISM: Mus musculus

<400> SEQUENCE: 46

Gln His His Tyr Gly Ile Pro Phe Thr
1               5

<210> SEQ ID NO 47
<211> LENGTH: 170
<212> TYPE: PRT
<213> ORGANISM: Homo sapiens

<400> SEQUENCE: 47

Arg Ala Val Pro Gly Gly Ser Ser Pro Ala Trp Thr Gln Cys Gln Gln
1               5                   10                  15

Leu Ser Gln Lys Leu Cys Thr Leu Ala Trp Ser Ala His Pro Leu Val
                20                  25                  30

Gly His Met Asp Leu Arg Glu Glu Gly Asp Glu Glu Thr Thr Asn Asp
            35                  40                  45

Val Pro His Ile Gln Cys Gly Asp Gly Cys Asp Pro Gln Gly Leu Arg

```
                50                  55                  60
Asp Asn Ser Gln Phe Cys Leu Gln Arg Ile His Gln Gly Leu Ile Phe
 65                  70                  75                  80

Tyr Glu Lys Leu Leu Gly Ser Asp Ile Phe Thr Gly Glu Pro Ser Leu
                 85                  90                  95

Leu Pro Asp Ser Pro Val Gly Gln Leu His Ala Ser Leu Leu Gly Leu
                100                 105                 110

Ser Gln Leu Leu Gln Pro Glu Gly His His Trp Glu Thr Gln Gln Ile
                115                 120                 125

Pro Ser Leu Ser Pro Ser Gln Pro Trp Gln Arg Leu Leu Leu Arg Phe
                130                 135                 140

Lys Ile Leu Arg Ser Leu Gln Ala Phe Val Ala Val Ala Ala Arg Val
145                 150                 155                 160

Phe Ala His Gly Ala Ala Thr Leu Ser Pro
                165                 170

<210> SEQ ID NO 48
<211> LENGTH: 175
<212> TYPE: PRT
<213> ORGANISM: Mus musculus

<400> SEQUENCE: 48

Val Pro Arg Ser Ser Pro Asp Trp Ala Gln Cys Gln Gln Leu Ser
 1               5                  10                  15

Arg Asn Leu Cys Met Leu Ala Trp Asn Ala His Ala Pro Ala Gly His
                 20                  25                  30

Met Asn Leu Leu Arg Glu Glu Asp Glu Glu Thr Lys Asn Asn Val
                 35                  40                  45

Pro Arg Ile Gln Cys Glu Asp Gly Cys Asp Pro Gln Gly Leu Lys Asp
 50                  55                  60

Asn Ser Gln Phe Cys Leu Gln Arg Ile Arg Gln Gly Leu Ala Phe Tyr
 65                  70                  75                  80

Lys His Leu Leu Asp Ser Asp Ile Phe Lys Gly Glu Pro Ala Leu Leu
                 85                  90                  95

Pro Asp Ser Pro Met Glu Gln Leu His Thr Ser Leu Leu Gly Leu Ser
                100                 105                 110

Gln Leu Leu Gln Pro Glu Asp His Pro Arg Glu Thr Gln Gln Met Pro
                115                 120                 125

Ser Leu Ser Ser Ser Gln Gln Trp Gln Arg Pro Leu Leu Arg Ser Lys
130                 135                 140

Ile Leu Arg Ser Leu Gln Ala Phe Leu Ala Ile Ala Ala Arg Val Phe
145                 150                 155                 160

Ala His Gly Ala Ala Thr Leu Thr Glu Pro Leu Val Pro Thr Ala
                165                 170                 175

<210> SEQ ID NO 49
<211> LENGTH: 1398
<212> TYPE: DNA
<213> ORGANISM: Artificial Sequence
<220> FEATURE:
<223> OTHER INFORMATION: Human constant and framework regions, rodent
      CDRs

<400> SEQUENCE: 49
atggctgtgc tgggctgct gttctgcctg gtgacattcc caagctgtgt gctgtcccag      60
gtgcagctgg tgcagtctgg cgctgaggtg aagaagcctg gcgcctccgt gaaggtctcc    120
tgcaaggctt ctggctacat cttcatcacc tactggatga cctgggtgcg gcaggcccct    180
```

```
ggccagggc tggagtggat gggccagatc ttccctgcca gcggctctgc agactacaac    240
gagaagttcg aaggcagagt caccatgacc acagacacat ccaccagcac agcctacatg    300
gagctgagga gcctgagatc tgacgacacc gccgtgtatt actgtgccag aggcggtggc    360
ggattcgctt actggggcca gggcaccctg gtcaccgtct ccagcgctag caccaagggc    420
ccatcggtct tccccctggc acctcctcc aagagcacct ctgggggcac agcggccctg    480
ggctgcctgg tcaaggacta cttccccgaa ccggtgacgg tgtcgtggaa ctcaggcgcc    540
ctgaccagcg gcgtgcacac cttcccggct gtcctacagt cctcaggact ctactccctc    600
agcagcgtgg tgaccgtgcc ctccagcagc ttgggcaccc agacctacat ctgcaacgtg    660
aatcacaagc ccagcaacac caaggtggac aagaaagttg agcccaaatc ttgtgacaaa    720
actcacacat gcccaccgtg cccagcacct gaactcctgg ggggaccgtc agtcttcctc    780
ttccccccaa acccaagga caccctcatg atctcccgga cccctgaggt cacatgcgtg    840
gtggtggacg tgagccacga agaccctgag gtcaagttca actggtacgt ggacggcgtg    900
gaggtgcata atgccaagac aaagccgcgg gaggagcagt acaacagcac gtaccgtgtg    960
gtcagcgtcc tcaccgtcct gcaccaggac tggctgaatg gcaaggagta caagtgcaag   1020
gtctccaaca agccctccc agccccatc gagaaaacca tctccaaagc caaagggcag   1080 cccccgagaac cacaggtgta caccctgccc ccatcccggg atgagctgac caagaaccag   1140
gtcagcctga cctgcctggt caaaggcttc tatcccagcg acatcgccgt ggagtgggag   1200
agcaatgggc agccggagaa caactacaag accacgcctc ccgtgctgga ctccgacggc   1260
tccttcttcc tctacagcaa gctcaccgtg gacaagagca ggtggcagca ggggaacgtc   1320
ttctcatgct ccgtgatgca tgaggctctg cacaaccact acacgcagaa gagcctctcc   1380
ctgtctccgg gtaaatga                                                 1398

<210> SEQ ID NO 50
<211> LENGTH: 702
<212> TYPE: DNA
<213> ORGANISM: Artificial Sequence
<220> FEATURE:
<223> OTHER INFORMATION: Human constant and framework regions, rodent
      CDRs

<400> SEQUENCE: 50
atggctccag tgcagctgct ggggctgctg gtgctgttcc tgccagccat gagatgtgat     60
atccagatga cccagtctcc atcctccctg tctgcctctg tgggcgacag agtgaccatc    120
acctgcagga ccagcgagaa catctacagc tacctggcct ggtatcagca gaagccaggg    180
aaggccccta gctgctgat ctataacgcc aagaccctgg ctgaagggt gccatccagg    240 ttcagcggca gcggctctgg gacagacttc accctgacca tcagcagcct gcagcctgag    300
gacttcgcca cctactactg tcagcaccac tacggaattc cattcacctt cggccagggc    360
accaaggtgg agatcaagcg tacggtggct gcaccatctg tcttcatctt ccctccatct    420
gatgagcagc tgaagtctgg aactgcctcc gtggtgtgcc tgctgaataa cttctatccc    480
agagaggcca aggtgcagtg gaaggtggat aacgccctcc agagcggcaa ctcccaggag    540
agcgtgacag agcaggacag caaggacagc acctacagcc tgagcagcac cctgaccctg    600
agcaaagcag actacgagaa acacaaggtg tacgcctgcg aggtgaccca tcagggcctg    660
agcagccccg tgacaaagag cttcaacagg ggagagtgtt aa                      702
```